(12) United States Patent
Ackermann et al.

(10) Patent No.: US 7,442,791 B2
(45) Date of Patent: Oct. 28, 2008

(54) AMINOALKYLAMIDE SUBSTITUTED CYCLOHEXYL DERIVATIVES

(75) Inventors: Jean Ackermann, Riehen (CH); Johannes Aebi, Basel (CH); Henrietta Dehmlow, Grenzach-Wyhlen (DE); Georges Hirth, Colmar (FR); Hans-Peter Maerki, Basel (CH); Olivier Morand, Hegenheim (FR); Narendra Panday, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 667 days.

(21) Appl. No.: 10/942,154

(22) Filed: Sep. 16, 2004

(65) Prior Publication Data

US 2005/0065210 A1 Mar. 24, 2005

(30) Foreign Application Priority Data

Sep. 22, 2003 (EP) ................................. 03021128

(51) Int. Cl.
C07D 243/08 (2006.01)
A01N 43/00 (2006.01)
A61K 31/33 (2006.01)

(52) U.S. Cl. ...................................................... 540/575
(58) Field of Classification Search ........................ None
See application file for complete search history.

(56) References Cited

U.S. PATENT DOCUMENTS

| 5,495,048 A | 2/1996 | Aebi et al. |
| 5,574,071 A | 11/1996 | Aebi et al. |
| 5,637,771 A | 6/1997 | Aebi et al. |

FOREIGN PATENT DOCUMENTS

| EP | 0636367 | 2/1995 |
| WO | WO 00/52134 | 9/2000 |

OTHER PUBLICATIONS

"Type 1 Diabetes- Prevention", http://diabetes.webmd.com/tc/type-1-diabetes-prevention, accessed Dec. 11, 2007.*
Diabetes Insipidus, http://www.nlm.nih.gov/cgi/mesh/2008/MB_cgi, accessed Dec. 11, 2007.*
"Diabetes Mellitus", http://www.nlm.nih.gov/cgi/mesh/2008/MB_cgi, accessed Dec. 11, 2007.*
"Vascular Diseases", http://www.nlm.nih.gov/cgi/mech/2008/MB_cgi, accessed Dec. 11, 2007.*
"Mycoses", http://www.nlm.nih.gov/cgi/mesh/2008/MB_cgi, accessed Dec. 11, 2007.*
"Parasitic Diseases", http://www.nlm.nih.gov/cgi/mesh/2008/MB_cgi, accessed Dec. 11, 2007.*
"Neoplasms", http://www.nlm.nih.gov/cgi/mesh/2008/MB_cgi, accessed Dec. 11, 2007.*
Suntory Ltd., Patent Abstracts of Japan, vol. 018, No. 347 (C1219), (1994) & JP 06 087810 A (1994) abstract & JP 06 087810 A, (1994), p. 31, line 40, pp. 32-34.
He Wei et al., Bioorganic & Medicinal Chemistry Letters, Potent quinoxaline-based inhibitors of PDGF receptor tyrosine kinase activity. Part 2: the sythesis and biological activities of RPR127963, an orally bioavailable inhibitor, (2003), 13 (18), pp. 3097-3100, Table 1 (compound 23a) Coden BMCLE8; ISSN:0960-894X, XP002317572.
Okano A. et al., Journal of Medicinal Chemistry (1972), 15(30), pp. 247-255, Table III (compound 23) Coden JMCMAR; ISSN:0022-2623, XP002317573.

* cited by examiner

Primary Examiner—James O. Wilson
Assistant Examiner—Noble Jarrell
(74) Attorney, Agent, or Firm—George W. Johnston; Patricia S. Rocha-Tramaloni

(57) ABSTRACT

The present invention relates to compounds of formula I

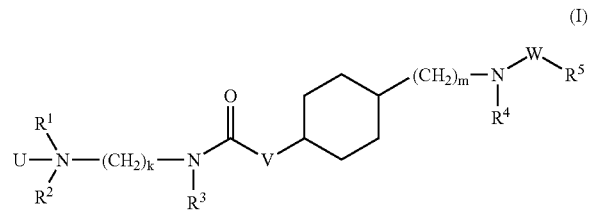

wherein $R^1$, $R^2$, $R^3$, $R^4$, $R^5$, U, V, W, k and m are as defined in the description and claims, and pharmaceutically acceptable salts and/or pharmaceutically acceptable esters thereof. The compounds are useful for the treatment and/or prophylaxis of diseases which are associated with 2,3-oxidosqualene-lanosterol cyclase such as hypercholesterolemia, hyperlipemia, arteriosclerosis, vascular diseases, mycoses, parasit infections, gallstones, tumors and/or hyperproliferative disorders, and treatment and/or prophylaxis of impaired glucose tolerance and diabetes.

8 Claims, No Drawings

AMINOALKYLAMIDE SUBSTITUTED CYCLOHEXYL DERIVATIVES

FIELD OF THE INVENTION

The present invention is concerned with novel aminoalkylamide substituted cyclohexyl derivatives, their manufacture and their use as medicaments. In particular, the invention relates to compounds of the formula I

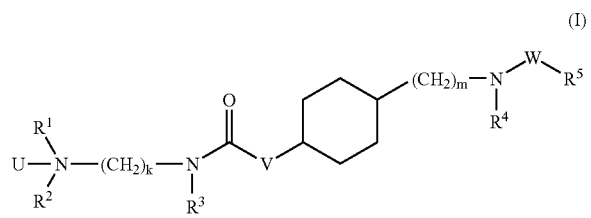

wherein
U,V,W,$R^1$,$R^2$,$R^3$,$R^4$,$R^5$,k and m and pharmaceutically acceptable salts and/or pharmaceutically acceptable esters thereof are described herein.

BACKGROUND OF THE INVENTION

The compounds of the present invention inhibit 2,3-oxidosqualene-lanosterol cyclase (EC 5.4.99.) which is required for the biosynthesis of cholesterol, ergosterol and other sterols. Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established [Gotto et al., Circulation 81:1721-1733 (1990); Stein et al., Nutr. Metab. Cardiovasc. Dis. 2:113-156 (1992); Illingworth, Med. Clin. North. Am. 84:23-42 (2000)]. Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C [Ross et al., Arch. Intern. Med. 159:1793-1802 (1999).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fib rate proved to be very efficacious in lowering LDL-C and triglycerides [Ellen and McPherson, J. Cardiol. 81:60B-65B (1998)], but safety of such a combination remains an issue [Shepherd, Eur. Heart J. 16:5-13 (1995) ]. A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses [Davignon et al., Can. J. Cardiol. 8:843-864 (1992); Pederson and Tobert, Drug Safety 14:11-24 (1996)].

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug [Morand et al., J. Lipid Res. 38:373-390 (1997); Mark et al., J. Lipid Res. 37:148-158 (1996)]. OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content [Morand et al., J. Lipid Res. 38:373-390 (1997)]. The compounds described in EP 636,367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol [Peffley et al., Biochem. Pharmacol. 56:439-449 (1998); Nelson et al., J. Biol. Chem. 256:1067-1068 (1981); Spencer et al., J. Biol. Chem. 260:13391-13394 (1985); Panini et al., J. Lipid Res. 27:1190-1204 (1986); Ness et al., Arch. Biochem. Biophys. 308:420-425 (1994)]. This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR [Janowski et al., Proc. Natl. Acad. Sci. USA 96:266-271 (1999)]. Considering that 24(S),25-epoxycholesterol is a by-product of inhibition of OSC it is hypothesized that the OSC inhibitors of the present invention could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels [Venkateswaran et al., J. Biol. Chem. 275: 14700-14707 (2000); Ordovas, Nutr Rev 58:76-79 (2000), Schmitz and Kaminsky, Front Biosci 6:D505-D514 (2001)], and/or inhibit intestinal cholesterol absorption [Mangelsdorf, XIIth International Symposium on Atherosclerosis, Stockholm, June 2000)]. In addition, possible cross talks between fatty acid and cholesterol metabolism mediated by liver LXR have been hypothesized [Tobin et al., Mol. Endocrinol. 14:741-752 (2000)].

SUMMARY OF THE INVENTION

The present invention provides compounds of the formula I

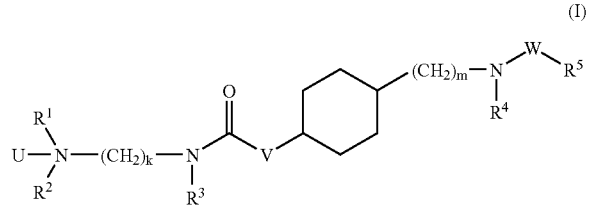

wherein
U is O or a lone pair;
$R^1$ is lower-alkyl, hydroxy-lower-alkyl, cycloalkyl or lower-alkyl-NH—C(O)—O-lower-alkyl;
$R^2$ is lower-alkyl or hydroxy-lower-alkyl;
$R^3$ is hydrogen, lower-alkyl, fluoro-lower-alkyl, or cycloalkyl; or
$R^2$ and $R^3$ are bonded to each other to form a ring together with the N—$(CH_2)_k$—N group to which they are attached and —$R^2$—$R^3$— is lower-alkylene;
$R^4$ is lower-alkyl;
$R^5$ is aryl or heteroaryl;
W is a single bond, CO, COO, $CONR^6$, CSO, $CSNR^6$, $SO_2$, or $SO_2NR^6$;
$R^6$ is hydrogen or lower-alkyl;
V is a single bond, lower-alkylene, or lower-alkylene-oxy;
k is 2, 3, or 4;
m is 0, 1, 2, or 3, wherein k+m is not more than 5;

and pharmaceutically acceptable salts and/or pharmaceutically acceptable esters thereof.

The present compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

DETAILED DESCRIPTION OF THE INVENTION

The present invention relates to compounds of the formula

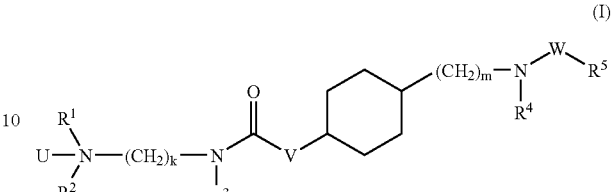

wherein
U is O or a lone pair;
$R^1$ is lower-alkyl, hydroxy-lower-alkyl, cycloalkyl or lower-alkyl-NH—C(O)—O-lower-alkyl;
$R^2$ is lower-alkyl or hydroxy-lower-alkyl;
$R^3$ is hydrogen, lower-alkyl, fluoro-lower-alkyl, or cycloalkyl; or
$R^2$ and $R^3$ are bonded to each other to form a ring together with the N—$(CH_2)_k$—N group to which they are attached and —$R^2$—$R^3$— is lower-alkylene;
$R^4$ is lower-alkyl;
$R^5$ is aryl or heteroaryl;
W is a single bond, CO, COO, $CONR^6$, CSO, $CSNR^6$, $SO_2$, or $SO_2NR^6$;
$R^6$ is hydrogen or lower-alkyl;
V is a single bond, lower-alkylene, or lower-alkylene-oxy;
k is 2, 3, or 4;
m is 0, 1, 2, or 3, wherein k+m is not more than 5;

and pharmaceutically acceptable salts and/or pharmaceutically acceptable esters thereof.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "fluoro-lower-alkyl" refers to lower-alkyl groups which are mono- or multiply substituted with fluorine, preferably with up to 6 fluorine atoms. Examples of fluoro-lower-alkyl groups are e.g. $CF_3$, $CF_3CH_2$ and $(CF_3)_2CH$.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl. The term "thio-alkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms, more preferrably up to 10 carbon atoms. Lower-alkenyl groups as described below also are preferred alkenyl groups. The term "lower-alkenyl" refers to a straight-chain or branched hydrocarbon residue comprising an olefinic bond and up to 7, preferably up to 4 carbon atoms, such as e.g. 2-propenyl.

The term "alkynyl", alone or in combination with other groups, stands for a straight-chain or branched hydrocarbon residue comprising a triple bond and up to 20, preferably up to 16 carbon atoms, more preferably up to 10 carbon atoms. Lower-alkynyl groups as described below also are preferred alkynyl groups. The term "lower-alkynyl" refers to a straight-chain or branched hydrocarbon residue comprising a triple bond and up to 7, preferably up to 4 carbon atoms, such as e.g. 2-propinyl.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "alkylene-oxy" refers to the group R''—O—, wherein R'' is an alkylene. The term "lower-alkylene-oxy" refers to the group R''—O—, wherein R'' is a lower-alkylene.

The term "aryl" relates to the phenyl or naphthyl group, preferably the phenyl group, which can optionally be substituted by 1 to 3 substituents independently selected from the group consisting of lower-alkyl, fluoro-lower-alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl. Preferred substituents are halogen, fluoro-lower-alkyl, $CF_3$, CN, lower-alkyl and/or lower-alkoxy.

The term "heteroaryl" refers to an aromatic 5- or 6-membered ring which can comprise 1, 2 or 3 atoms selected from nitrogen, oxygen and/or sulphur, such as furyl, pyridyl, pyridazinyl, pyrimidinyl, pyrazinyl, thienyl, isoxazolyl, oxazolyl, imidazolyl, or pyrrolyl. A heteroaryl group may have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts are phosphates, citrates, fumarates, formates, hydrochlorides, hydrobromides and methanesulfonic acid salts.

The term "pharmaceutically acceptable esters" embraces esters of the compounds of formula (I), in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In one embodiment the present invention provides compounds of formula I, which are trans-isomers and which are characterized by formula Ia

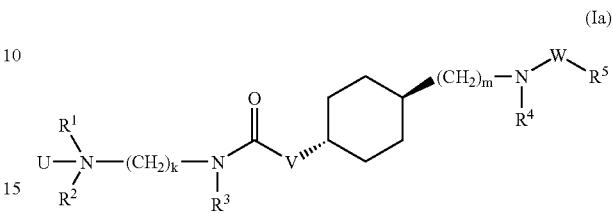

(Ia)

wherein $R^1$, $R^2$, $R^3$, $R^4$, $R^5$, U, V, W, k and m are as defined above, and pharmaceutically acceptable salts and/or pharmaceutically acceptable esters thereof.

Other preferred embodiments relate to compounds of formula (I) wherein U is a lone pair.

Compounds as described above, in which $R^1$ is lower-alkyl, hydroxy-lower-alkyl or lower-alkyl-NH—C(O)—O-lower-alkyl, are preferred, particularly lower-alkyl or hydroxy-lower-alkyl, more particularly methyl or 2-hydroxy-ethyl.

Other preferred compounds of the present invention are those, wherein $R^2$ is lower-alkyl, particularly methyl, or hydroxy-lower-alkyl. Compounds in which $R^3$ is lower-alkyl, fluoro-lower-alkyl or cycloalkyl, are also preferred, particularly those wherein $R^3$ is lower-alkyl, more particularly methyl.

In a further preferred embodiment of the present invention, $R^2$ and $R^3$ are bonded to each other to form a ring together with the N—$(CH_2)_k$—N group to which they are attached and —$R^2$—$R^3$— is lower-alkylene. Preferably, —$R^2$—$R^3$— is —$(CH_2)_{2-4}$—, more preferably —$(CH_2)_2$— or —$(CH_2)_3$—. Compounds, in which $R^4$ is methyl are also preferred.

Further preferred compounds of the present invention are those, wherein W is $SO_2$ or COO and $R^5$ is aryl. In such compounds, $R^5$ is preferably phenyl substituted with fluoro-lower-alkyl or halogen. More preferably, $R^5$ is 4-trifluoromethyl-phenyl or 4-chloro-phenyl. Other preferred compounds are those, wherein W is a single bond and $R^5$ is heteroaryl, preferably $R^5$ is pyrimidinyl substituted with halogen, lower-alkyl or fluoro-lower-alkyl, more preferably $R^5$ is 5-bromo-pyrimidin-2-yl, 5-chloro-pyrimidin-2-yl or 4-trifluoromethyl-pyrimidin-2-yl.

In another preferred embodiment of the present invention, k is 2 or 3, preferably 2. Further, compounds in which m is 0, 1 or 2, are preferred. In such compounds, m=0, m=1, and m=2 individually constitute preferred embodiments.

Furthermore, compounds as defined above, in which V is a single bond or lower-alkyleneoxy, are preferred, particularly those, wherein V is a single bond, —$CH_2$—O— or —$(CH_2)_2$—O—.

Preferred compounds of general formula (I) are those selected from the group consisting of
trans-N-(2-Dimethylamino-ethyl)-N-methyl-3-{4-[methyl-(4-trifluoromethyl-benzenesulfonyl)-amino]-cyclohexyloxy}-propionamide,
trans-N-Methyl-N-{4-[3-(4-methyl-piperazin-1-yl)-3-oxo-propoxy]-cyclohexyl}-4-trifluoromethyl-benzene-sulfonamide,
trans-N-(2-Dimethylamino-ethyl)-N-methyl-2-{4-[methyl-(4-trifluoromethyl-benzenesulfonyl)-amino]-cyclohexyloxy}-acetamide, trans-N-Methyl-N-{4-[2-(4-methyl-piperazin-1-yl)-2-oxo-ethoxy]-cyclohexyl}-4-trifluoromethyl-benzenesulfonamide, trans-(4-{[(2-Dimethylamino-ethyl)-methyl-carbamoyl]-methoxy}-cyclohexyl)-methyl-carbamic acid 4-bromo-phenyl ester, trans-(4-{[(2-Dimethylamino-ethyl)-methyl-carbamoyl]-methoxy}-cyclohexyl)-methyl-carbamic acid 4-chloro-phenyl ester, trans-4-[Methyl-(4-trifluoromethyl-benzenesulfonyl)-amino]-cyclohexanecarboxylic acid (2-dimethylamino-ethyl)-methyl-amide, trans-4-[Methyl-(4-trifluoromethyl-benzenesulfonyl)-amino]-cyclohexanecarboxylic acid (3-dimethylamino-propyl)-methyl-amide, trans-{4-[(2-Dimethylamino-ethyl)-methyl-carbamoyl]-cyclohexylmethyl}-methyl-carbamic acid 4-chloro-phenyl ester, trans-{4-[(3-Dimethylamino-propyl)-methyl-carbamoyl]-cyclohexylmethyl}-methyl-carbamic acid 4-chloro-phenyl ester, trans-(2-{4-[(2-Dimethylamino-ethyl)-methyl-carbamoyl]-cyclohexyl}-ethyl)-methyl-carbamic acid 4-chloro-phenyl ester, trans-(2-{4-[4-(2-Hydroxy-ethyl)-[1,4]diazepane-1-carbonyl]-cyclohexyl}-ethyl)-methyl-carbamic acid 4-chloro-phenyl ester, trans-4-{[(5-Bromo-pyrimidin-2-yl)-methyl-amino]-methyl}-cyclohexanecarboxylic acid (2-dimethylamino-ethyl)-methyl-amide, trans-4-{[(5-Bromo-pyrimidin-2-yl)-methyl-amino]-methyl}-cyclohexanecarboxylic acid (3-dimethylamino-propyl)-methyl-amide, trans-(4-{[(5-Bromo-pyrimidin-2-yl)-methyl-amino]-methyl}-cyclohexyl)-(4-methyl-[1,4]diazepan-1-yl)-methanone, trans-(4-{[(5-Bromo-pyrimidin-2-yl)-methyl-amino]-methyl}-cyclohexyl)-[4-(2-hydroxy-ethyl)-[1,4]diazepan-1-yl]-methanone, trans-4-{2-[(5-Bromo-pyrimidin-2-yl)-methyl-amino]-ethyl}-cyclohexanecarboxylic acid (2-dimethylamino-ethyl)-methyl-amide, trans-(4-{2-[(5-Bromo-pyrimidin-2-yl)-methyl-amino]-ethyl}-cyclohexyl)-(4-methyl-[1,4]diazepan-1-yl) -methanone, trans-(4-{2-[(5-Bromo-pyrimidin-2-yl)-methyl-amino]-ethyl}-cyclohexyl)-[4-(2-hydroxy-ethyl)-[1,4]diazepan-1-yl]-methanone, trans-Butyl-carbamic acid 2-[4-(4-{2-[(5-bromo-pyrimidin-2-yl)-methyl-amino]-ethyl}-cyclohexanecarbonyl)-[1,4]diazepan-1-yl]-ethyl ester, trans-4-{[(5-Ethyl-pyrimidin-2-yl) -methyl-amino]-methyl}-cyclohexanecarboxylic acid (2-dimethylamino-ethyl)-methyl-amide, trans-(4-{[(5-Ethyl-pyrimidin-2-yl)-methyl-amino]-methyl}-cyclohexyl)-[4-(2-hydroxy-ethyl)-[1,4]diazepan-1-yl]-methanone, trans-(4-{2-[(5-Ethyl-pyrimidin-2-yl)-methyl-amino]-ethyl}-cyclohexyl)-[4-(2-hydroxy-ethyl)-[1,4]diazepan-1-yl]-methanone, trans-[4-(2-Hydroxy-ethyl)-[1,4]diazepan-1-yl]-(4-{2-[methyl-(5-propyl-pyrimidin-2-yl)-amino]-ethyl}-cyclohexyl)-methanone, trans-4-{2-[(5-Chloro-pyrimidin-2-yl)-methyl-amino]-ethyl}-cyclohexanecarboxylic acid (2-dimethylamino-ethyl)-methyl-amide, trans-(4-{2-[(5-Chloro-pyrimidin-2-yl)-methyl-amino]-ethyl}-cyclohexyl)-(4-methyl-[1,4]diazepan-1-yl)-methanone, trans-(4-{2-[(5-Chloro-pyrimidin-2-yl)-methyl-amino]-ethyl}-cyclohexyl)-[4-(2-hydroxy-ethyl)-[1,4]diazepan-1-yl]-methanone, trans-(4-Methyl-[1,4]diazepan-1-yl)-(4-{2-[methyl-(4-trifluoromethyl-pyrimidin-2-yl)-amino]-ethyl}-cyclohexyl)-methanone, trans-4-{[(5-Bromo-pyrimidin-2-yl)-methyl-amino]-methyl}-cyclohexanecarboxylic acid cyclopropyl-(2-dimethylamino-ethyl)-amide, trans-4-{[(5-Ethyl-pyrimidin-2-yl)-methyl-amino]-methyl}-cyclohexanecarboxylic acid cyclopropyl-(2-dimethylamino-ethyl)-amide, trans-4-{[(5-Ethyl-pyrimidin-2-yl)-methyl-amino]-methyl}-cyclohexanecarboxylic acid (2-dimethylamino-ethyl)-(2,2,2-trifluoro-ethyl)-amide, trans-4-{2-[(5-Bromo-pyrimidin-2-yl)-methyl-amino]-ethyl}-cyclohexanecarboxylic acid {2-[ethyl-(2-hydroxy-ethyl)-amino]-ethyl}-methyl-amide, trans-4-{2-[Methyl-(5-propyl-pyrimidin-2-yl)-amino]-ethyl}-cyclohexanecarboxylic acid {2-[ethyl-(2-hydroxy-ethyl)-amino]-ethyl}-methyl-amide, trans-4-{2-[(5-Chloro-pyrimidin-2-yl)-methyl-amino]-ethyl}-cyclohexanecarboxylic acid {2-[ethyl-(2-hydroxy-ethyl)-amino]-ethyl}-methyl-amide, trans-4-{[(5-Ethyl-pyrimidin-2-yl)-methyl-amino]-methyl}-cyclohexanecarboxylic acid {2-[ethyl-(2-hydroxy-ethyl)-amino]-ethyl}-methyl-amide, trans-4-{2-[(5-Bromo-pyrimidin-2-yl)-methyl-amino]-ethyl}-cyclohexanecarboxylic acid {2-[bis-(2-hydroxy-ethyl)-amino]-ethyl}-methyl-amide, trans-4-{2-[(5-Chloro-pyrimidin-2-yl)-methyl-amino]-ethyl}-cyclohexanecarboxylic acid {2-[bis-(2-hydroxy-ethyl)-amino]-ethyl}-methyl-amide, trans-{4-[(2-Dimethylamino-ethyl)-methyl-carbamoyl]-cyclohexyl}-methyl-carbamic acid 4-chloro-phenyl ester, trans-4-[(5-Bromo-pyrimidin-2-yl)-methyl-amino]-cyclohexanecarboxylic acid (2-dimethylamino-ethyl)-methyl-amide, trans-N-Methyl-N-[4-(4-methyl-piperazine-1-carbonyl)-cyclohexylmethyl]-4-trifluoromethyl-benzenesulfonamide, trans-4-{[Methyl-(4-trifluoromethyl-benzenesulfonyl)-amino]-methyl}-cyclohexanecarboxylic acid (2-dimethylamino-ethyl)-methyl-amide, trans-N-(2-Dimethylamino-ethyl)-N-methyl-3-(4-{[methyl-(4-trifluoromethyl-benzenesulfonyl)-amino]-methyl}-cyclohexyl)-propionamide, trans-N-(2-Dimethylamino-ethyl)-N-methyl-2-{4-[methyl-(4-trifluoromethyl-benzenesulfonyl)-amino]-cyclohexyloxy}-propionamide, and trans-N-(2-Dimethylamino-ethyl)-2,N-dimethyl-2-{4-[methyl-(4-trifluoromethyl-benzenesulfonyl)-amino]-cyclohexyloxy}-propionamide, and pharmaceutically acceptable salts and/or pharmaceutically acceptable esters thereof.

Particularly preferred compounds of general formula (I) are those selected from the group consisting of trans-N-(2-Dimethylamino-ethyl)-N-methyl-3-{4-[methyl-(4-trifluoromethyl-benzenesulfonyl)-amino]-cyclohexyloxy}-propionamide, trans-N-Methyl-N-{4-[3-(4-methyl-piperazin-1-yl)-3-oxo-propoxy]-cyclohexyl}-4-trifluoromethyl-benzenesulfonamide, trans-(4-{[(2-Dimethylamino-ethyl)-methyl-carbamoyl]-methoxy}-cyclohexyl)-methyl-carbamic acid 4-chloro-phenyl ester, trans-(2-{4-[(2-Dimethylamino-ethyl)-methyl-carbamoyl]-cyclohexyl}-ethyl)-methyl-carbamic acid 4-chloro-phenyl ester, trans-4-{[(5-Bromo-pyrimidin-2-yl)-methyl-amino]-methyl}-cyclohexanecarboxylic acid (2-dimethylamino-ethyl)-methyl-amide, trans-(4-{2-[(5-Bromo-pyrimidin-2-yl)-methyl-amino]-ethyl}-cyclohexyl)-(4-methyl-[1,4]diazepan-1-yl)-methanone, trans-(4-{2-[(5-Bromo-pyrimidin-2-yl)-methyl-amino]-ethyl}-cyclohexyl)-[4-(2-hydroxy-ethyl)-[1,4]diazepan-1-yl]-methanone, trans-(4-{2-[(5-Chloro-pyrimidin-2-yl)-methyl-amino]-ethyl}-cyclohexyl)-(4-methyl-[1,4]diazepan-1-yl)-methanone, and trans-(4-Methyl-[1,4]diazepan-1-yl)-(4-{2-[methyl-(4-trifluoromethyl-pyrimidin-2-yl)-amino]-ethyl}-cyclohexyl)-methanone and pharmaceutically acceptable salts and/or pharmaceutically acceptable esters thereof.

Compounds of formula (I) can have one or more asymmetric carbon atoms and can exist in the form of optically pure enantiomers or as racemates. They can exist as cis- or trans-isomers. The invention embraces all of these forms. Compounds of formula (I) which are trans-isomers (with reference to the cyclohexyl ring) are preferred.

It will be appreciated, that the compounds of general formula (I) in this invention may be derivatised at functional groups to provide derivatives which are capable of conversion back to the parent compound in vivo.

The present invention also relates to a process for the manufacture of compounds as described above, which process comprises reacting a compound of formula II

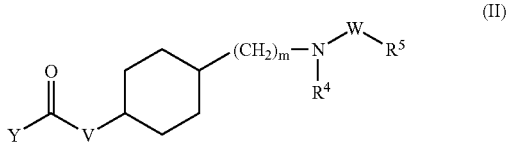

wherein $R^4, R^5$, V, W, and m have the significances given above and Y is a group OH, Cl, or Br, with $NR^1R^2(CH_2)_kNR^3H$, wherein $R^1$, $R^2$, $R^3$ and k have the significance given above, and optionally converting a compound of formula (I) as defined above to a pharmaceutically acceptable salt and or a pharmaceutically acceptable ester, and optionally converting a compound of formula (I) as defined above, wherein U is a lone pair, to a corresponding compound wherein U is O.

A process as defined above, without the optional conversion into a pharmaceutically acceptable salt and or a pharmaceutically acceptable ester and without the conversion of a compound of formula (I) as defined above, wherein U is a lone pair, to a corresponding compound wherein U is O, is preferred.

Reactions of a compound of formula (II) with a compound $NR^1R^2(CH_2)_kNR^3H$ can be carried out by procedures known in the art and as described in Scheme 3 (step c) or in scheme 9 (step c) with coupling reagents such as EDCI, HOBT, DCC, 2-chloro-1-methyl-pyridinium iodide or BOP and a base such as Huenig's base, $NEt_3$ or NMM in $CH_2Cl_2$, DMF, DMA or dioxane. Alternatively a two-step procedure might be used: treatment of the acid (II) with oxalyl chloride in $CH_2Cl_2$ in the presence of DMF, followed by reaction with the corresponding amine $NR^1R^2(CH_2)_kNR^3H$. A compound as defined above can be converted to a pharmaceutically acceptable salt by procedures known in the art such as by a treatment with a corresponding acid in a solvent like ethanol, methanol or dichloro-methane in a temperature range of e.g. −20° C. and +40° C. A compound as defined above can be converted to an ester by treatment of a compound with a hydroxyl moiety with the corresponding acid chloride or acid anhydride in the presence of DMAP in a solvent like $CH_2Cl_2$ or pyridine. A compound as defined above, wherein U is a lone pair can be converted to a compound wherein U is O by procedures known in the art such as by reaction with a mixture of hydrogen peroxide urea adduct and phthalic anhydride in dichloromethane at room temperature (RT).

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

Scheme 1
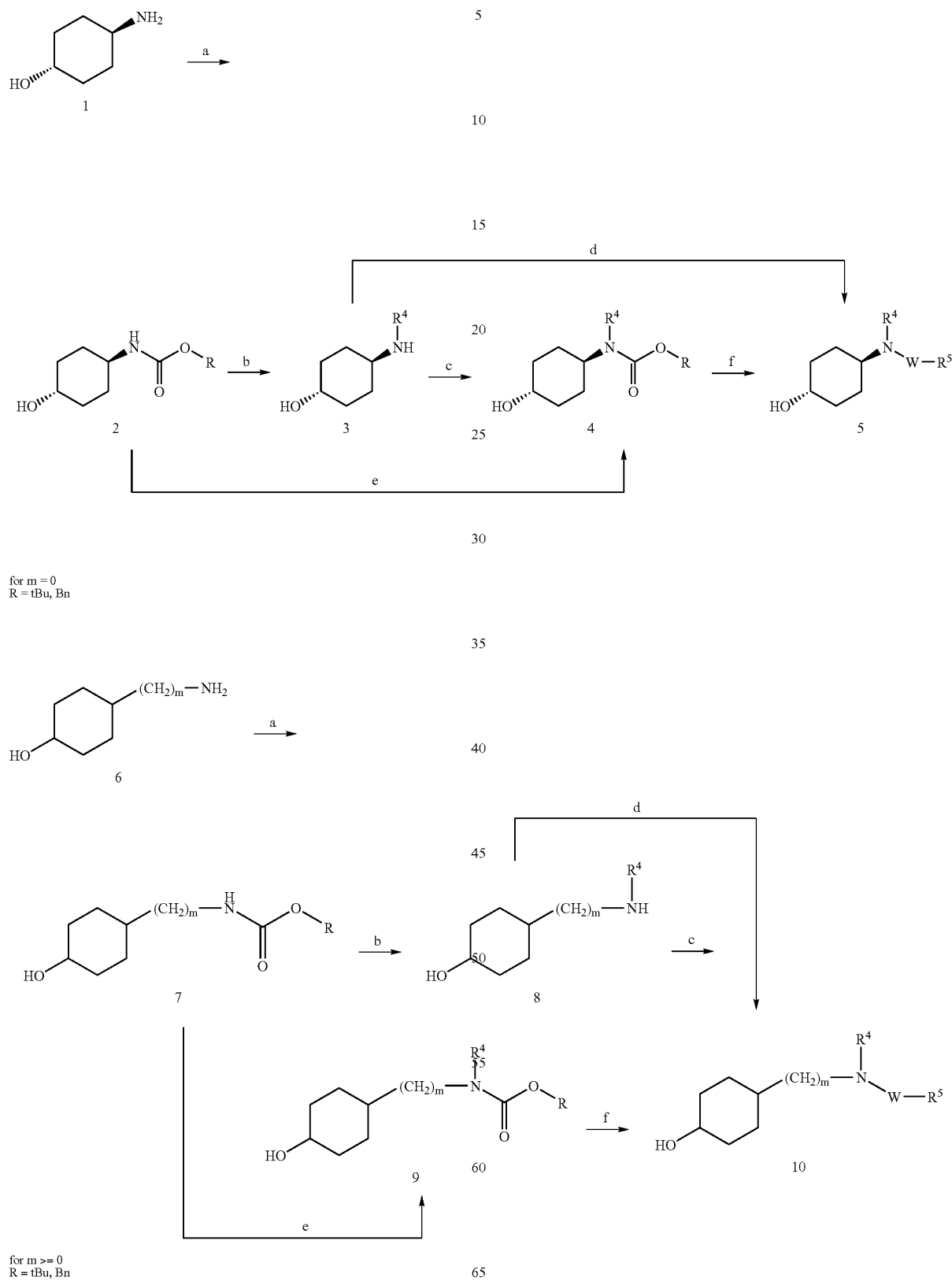
for m = 0
R = tBu, Bn
for m >= 0
R = tBu, Bn

Scheme 2
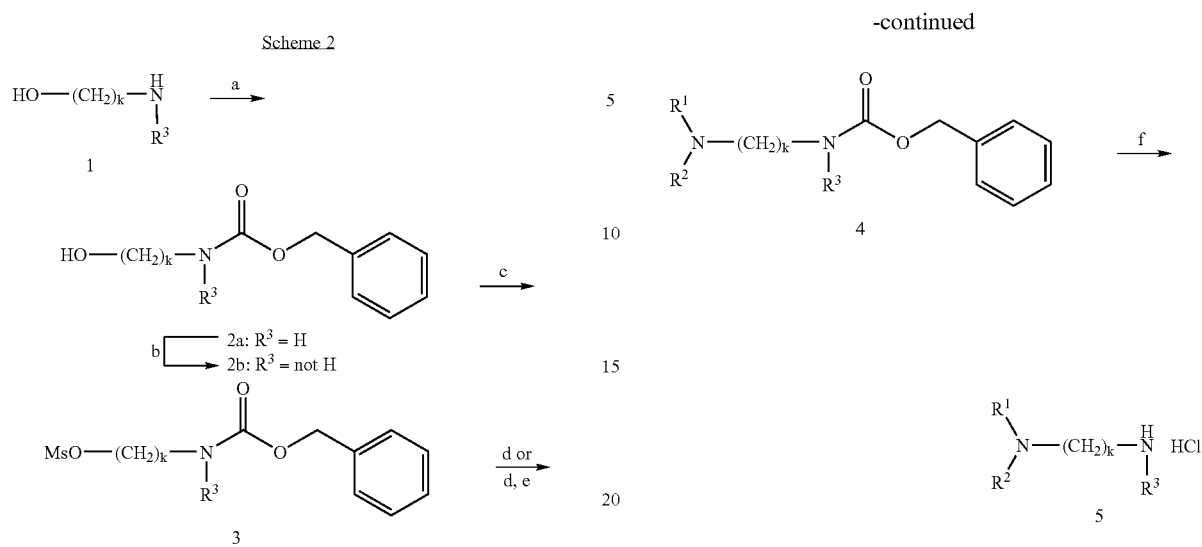
Scheme 3
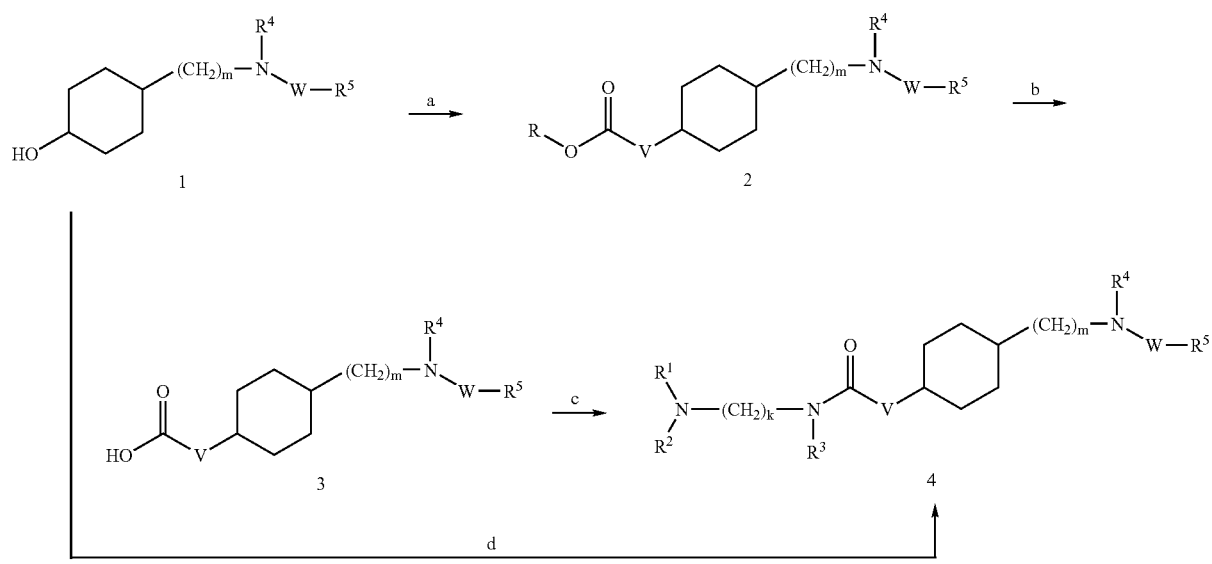
R = t Bu, alkyl
Scheme 4
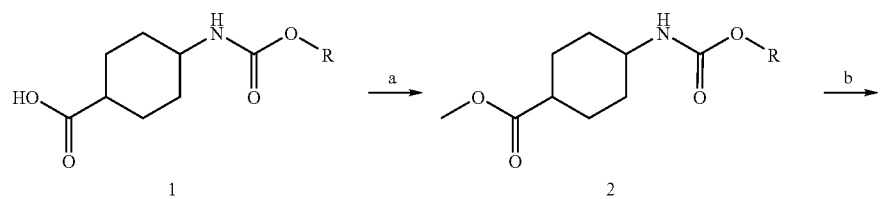

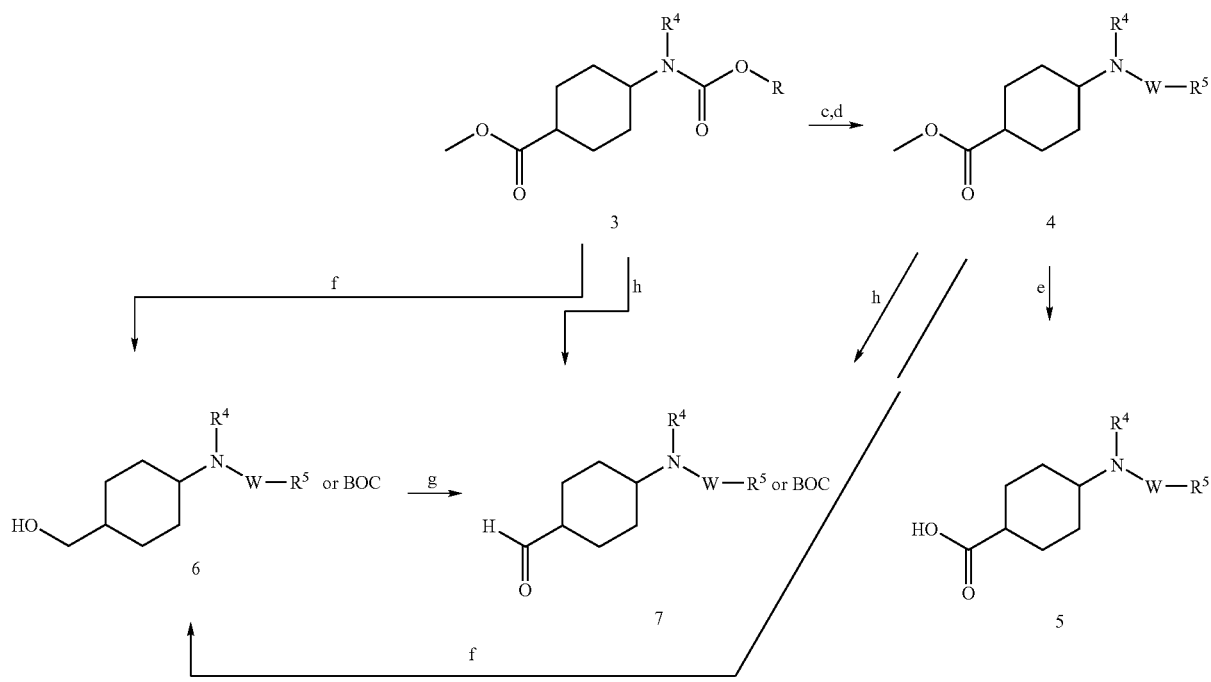
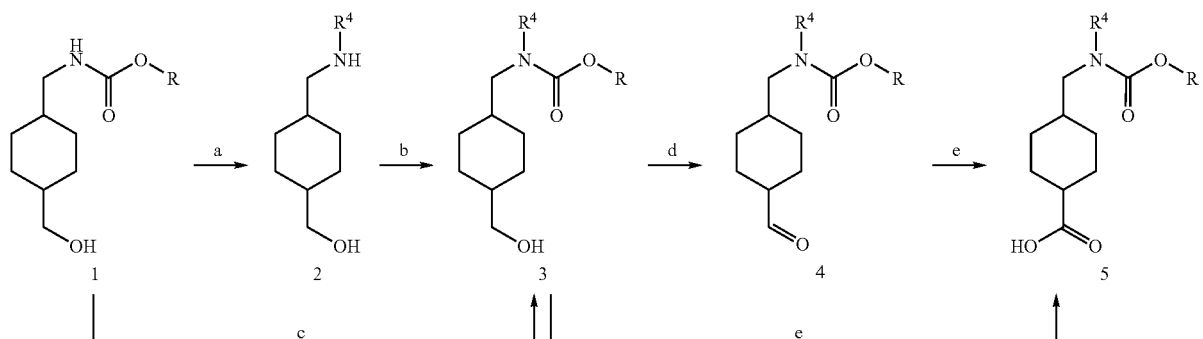
Scheme 5
R = tBu
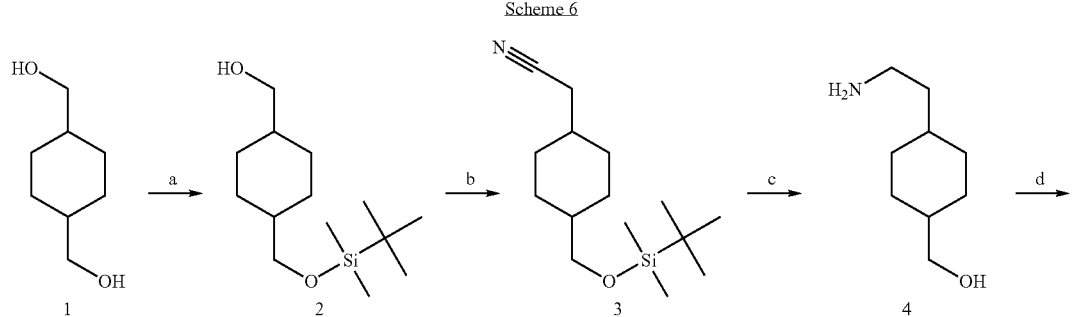
Scheme 6

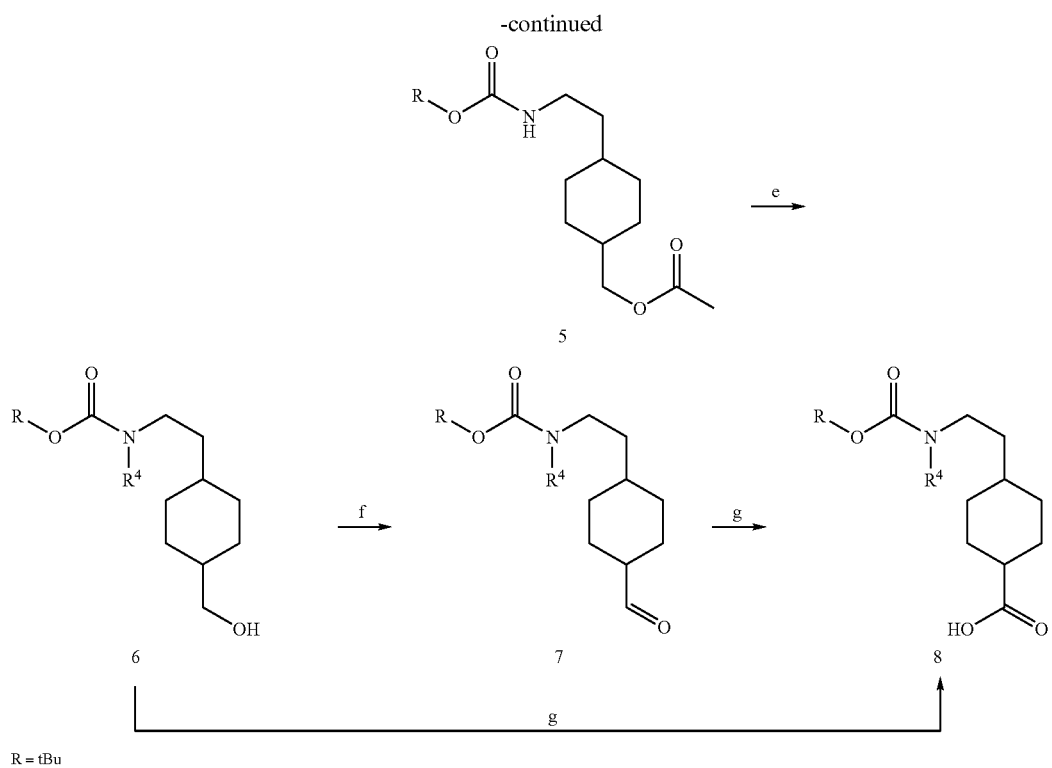
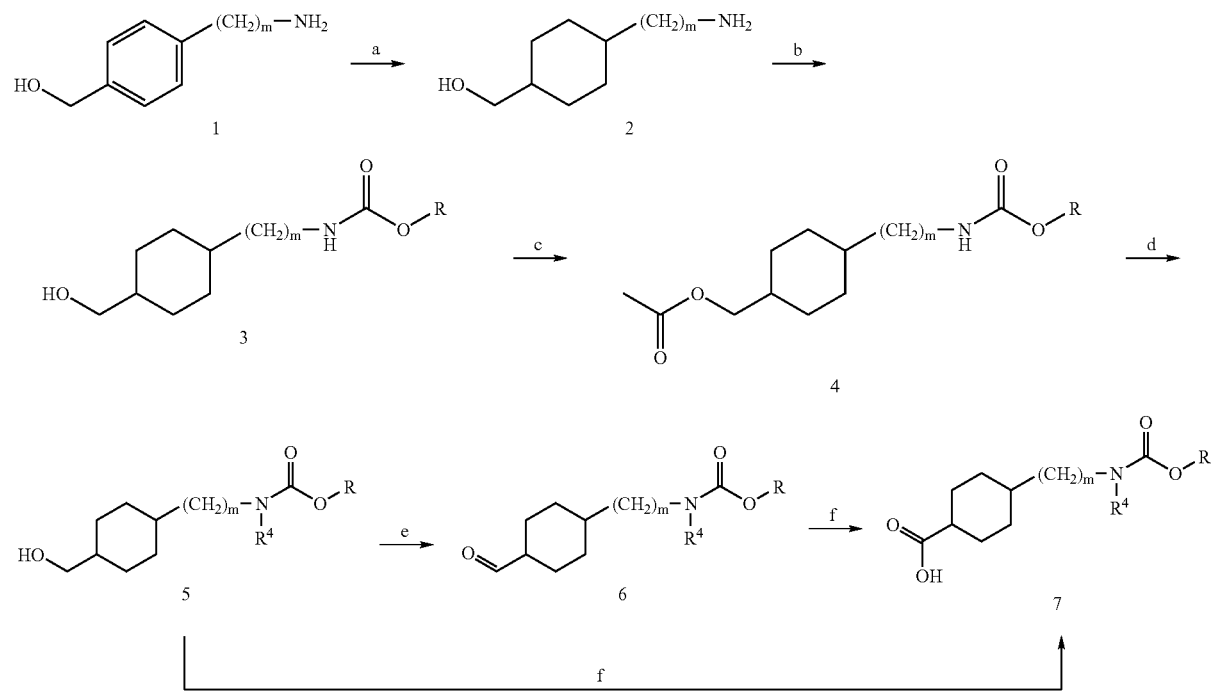
Scheme 7

Scheme 8
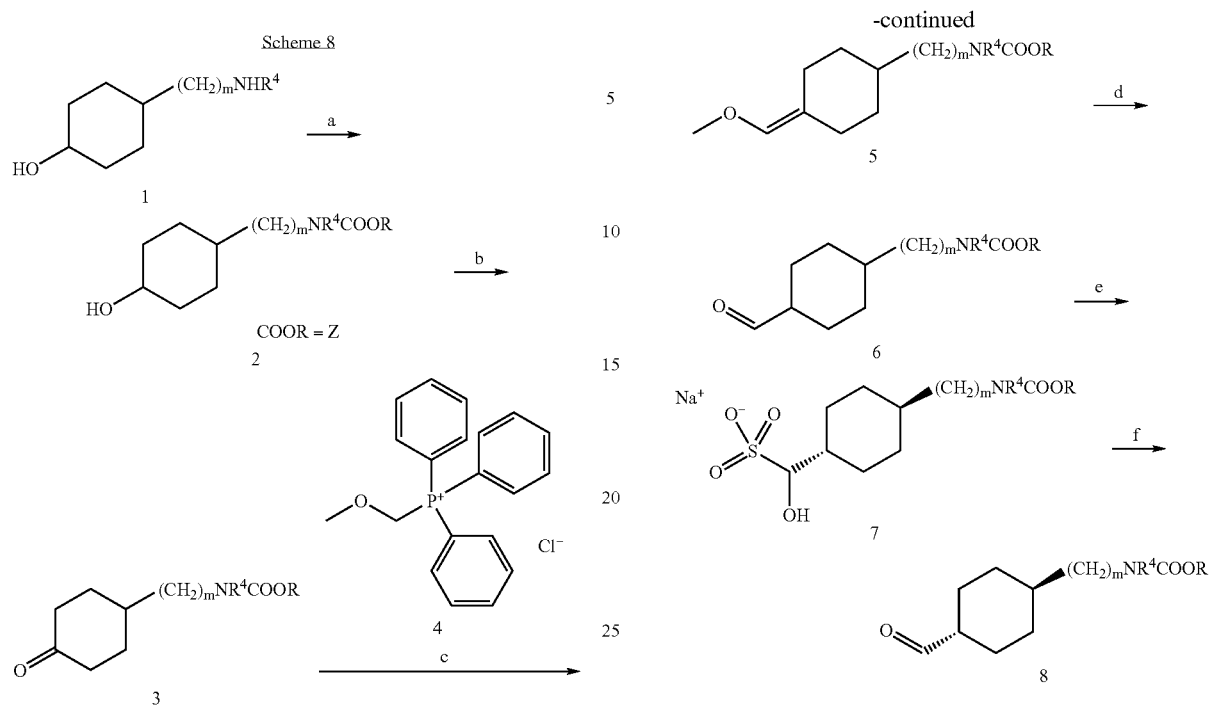
Scheme 9
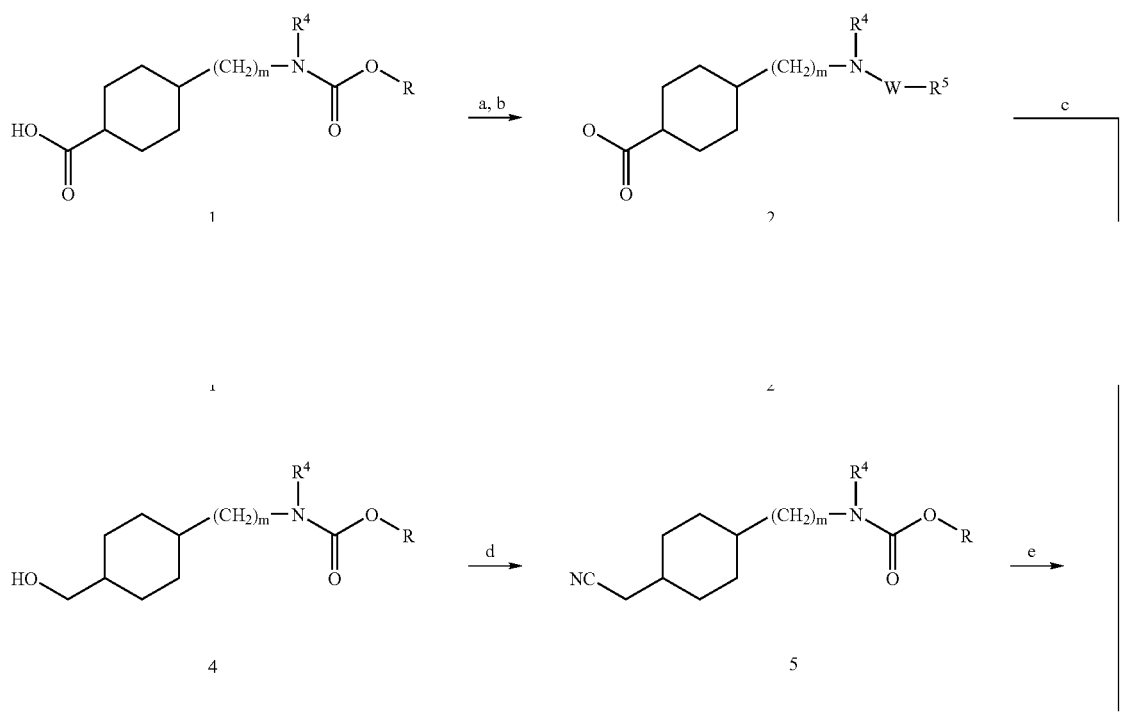

-continued

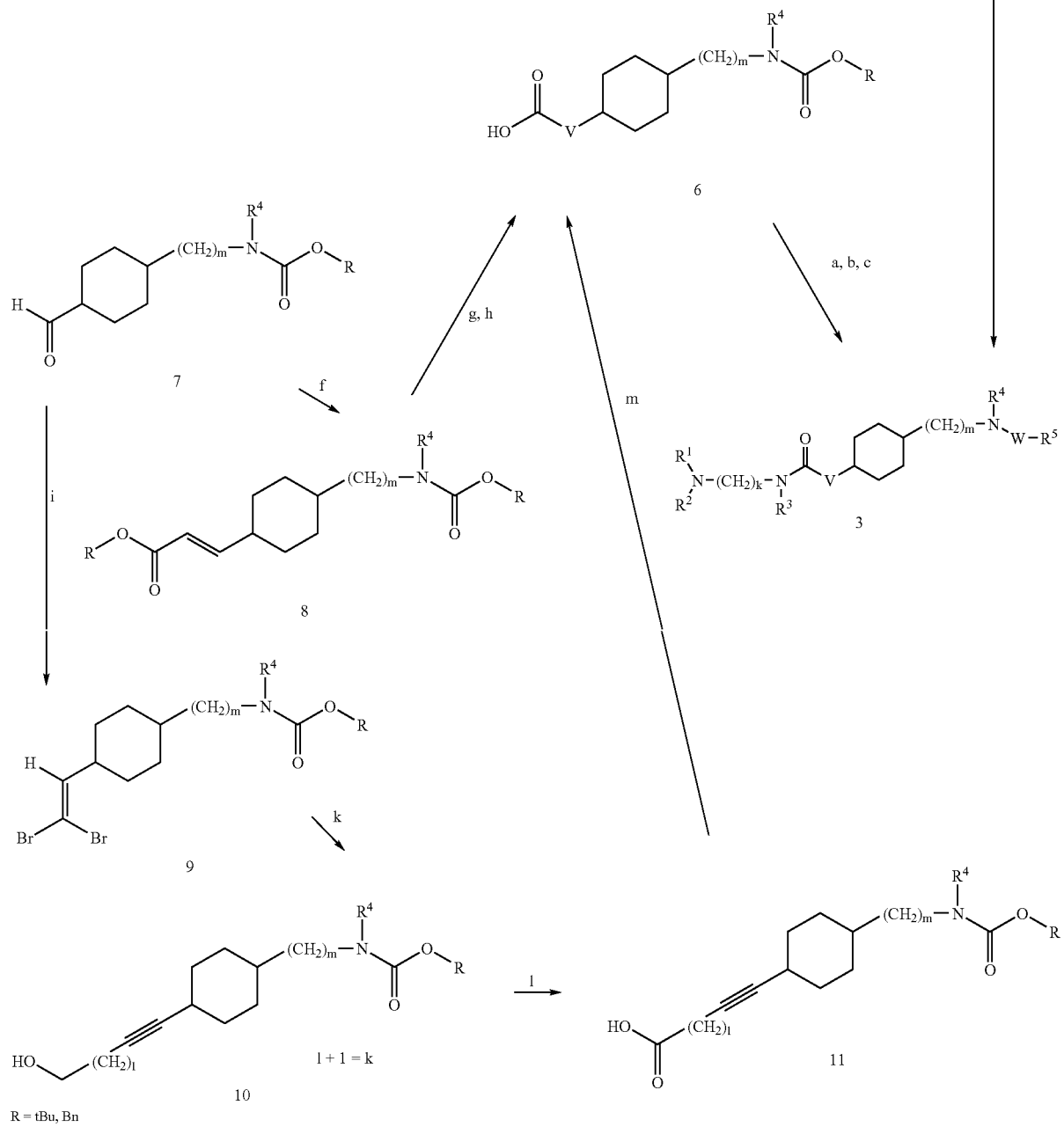

Scheme 1

The preparation of the starting materials for aminocyclohexyl derivatives of formula (I) in which V contains an oxygen is depicted in scheme 1. For compounds with m=0, the synthesis starts from trans-4-aminocyclohexanol 1 which is converted to the Z-derivative or the BOC derivative 2 e.g. ZCl, $Na_2CO_3$, THF, $H_2O$ or $(BOC)_2O$, iPrOH, $CH_2Cl_2$, respectively (step a). Lithium aluminum hydride reduction yields trans-4-methylaminocyclohexanol 3 which is either BOC-protected or Z-protected to yield compound 4 (step c) or is directly transferred (step d) into the desired $R^5$W-derivative 5 by using one of the methods described below. If needed, the aminocyclohexanol derivative can be treated with hexamethyldisilazane at reflux, prior to the introduction of the $R^5$W-moiety.

Sulfonamides: Sulfonylation of the amines is done in dioxane or $CH_2Cl_2$ with Huenig's base and a sulfonyl chloride over night at RT to yield the sulfonamide 5.

Carbamates: The amines may be reacted with $R^5OCOCl$/Huenig's base in dioxane or $CH_2Cl_2$. Alternatively, the chloroformates may be prepared in situ by treatment of $R^5OH$ with $Cl_3COCl$ in the presence of quinoline followed by reaction with the amines in the presence of Huenig's base.

Thiocarbamates: The amines may be reacted with $R^5OCSCl$ in dioxane.

Ureas: The amines may be reacted with isocyanate in dioxane at RT.

Thioureas: The amines may be reacted with isothiocyanate in dioxane at RT.

Amides: The amines may be reacted with $R^5COCl$/Huenig's base in $CH_2Cl_2$, $R^5COOH$/EDCI/DMAP (via formation of the symmetrical anhydride, and subsequent addition of the starting amine at $-10°$ C. to RT) or alternatively with $R^5COOH$/EDCI/DMAP or $R^5COOH$/Huenig's base or NMM/EDCI/HOBT in DMF, dioxane or $CH_2Cl_2$ at RT.

Sulfamides: The amines may be reacted with sulfamoyl chlorides in dioxane in the presence of an excess of triethylamine to yield sulfamide 5. The sulfamoyl chlorides can be prepared from $R^5NH_2$ and chlorosulfonic acid in $CH_2Cl_2$ at $0°$ C. to RT followed by reaction with $PCl_5$ in toluene at $75°$ C. Alternatively, the sulfamoyl chlorides can be synthesized in acetonitrile with $R^5NH_2$ and sulfuryl chloride at $0°$ C. to $65°$ C.

Heterocyles: For the preparation of compounds with W=single bond, $R^5$=heterocyle two different methods may be employed: Method A: The amines may be reacted with 2-halo-heteroaryl/N-ethyldiisopropylamine for 1 h to 5 days at 80 to $120°$ C. in DMA or no solvent, or Method B (for less reactive compounds): Reaction of amines with 2-halo-heteroaryl/N-ethyldiisopropylamine/CuI or NaI for 1-10 h at $120°$ C. or with microwave heating for 0.5 to 6 h at 120-150° C. in DMA.

Alternatively, the residue $R^4$ can be introduced via alkylation. Therefore, compound 2 can be first O-protected and then N-alkylated at the protected amino function with an alkyl derivative in the presence of a base like sodium hydride in a solvent like N,N-dimethyl-formamide, THF or acetonitrile at temperatures between RT and $80°$ C.; after O-deprotection the compound 4 is obtained (step e). BOC-deprotection (TFA, $CH_2Cl_2$) or Z-deprotection (hydrogenation) followed by treatment with $R^5W$-derivatives gives compounds of the formula 5 (step f).

For m>0, the aminocyclohexanol derivatives may be derived from the corresponding aminophenol, 4-hydroxybenzylamine, tyramine or 3-(4-hydroxyphenyl)propylamine by hydrogenation. These derivatives may be converted to the compounds of formula 10 as described for 5.

Scheme 2

The synthesis of amine building blocks is depicted in scheme 2. The hydroxyalkyl amines 1 can be converted to the Z-protected derivative 2a or 2b using benzylchloroformate and $Et_3N$ in $CH_2Cl_2$ (step a). In the case that $R^3$=H, other $R^3$ moieties may be introduced via alkylation. Therefore, compound 2a can be first O-protected (e.g. with AcCl in $CH_2Cl_2$, pyridine) and then N-alkylated with an alkyl derivative in the presence of a base like sodium hydride in a solvent like N,N-dimethylformamide, THF or acetonitrile at temperatures between RT and $80°$ C. and O-deprotected to give compound 2b (step b). Mesylation with methane sulfonyl chloride and pyridine in $CH_2Cl_2$ (step c) and treatment of the mesylate 3 with an amine $NR^1R^2H$ yields compound 4 (step d). In the case that $R^{1'}$ is hydrogen the desired residue $R^1$ may be introduced by alkylation with a reactive alkyl derivative, if necessary in the appropriate protected form (step e). In the case that the reaction was performed with an amine $NHR^{1'}R^{2'}$ in which $R^{1'}$ and/or $R^{2'}$ contain an ester moiety this can be reduced by e.g. $NaBH_4$ in solvents like THF or MeOH to the corresponding hydroxyalkyl derivatives. Deprotection of compound 4 can be achieved by hydrogenation with Pd/C in acidic MeOH or EtOH to yield the desired amines 5 (step f). For compounds in which $R^2$ and $R^3$ are bonded to each other to form a ring, these can be synthezised from derivatives 3 in which $R^3$ is a BOC-protected aminoalkyl. Deprotection (HCl in dioxane or TFA, $CH_2Cl_2$) followed by cyclization to compound 4 (step d). In the case that $R^{1'}$ is hydrogen, the desired residue $R^1$ may be introduced by alkylation with a reactive alkyl derivative, if necessary in the appropriate protected form (step e).

Scheme 3

The synthesis of compounds of formula (I) in which V is lower-alkylene-oxy is depicted in scheme 3. The amino-cyclohexanol derivative 1 can be treated under phase transfer conditions with e.g. ω-halo-alkylcarbonic acid tert butyl esters, NaOH, nBu4NHSO$_4$ to yield ester 2. Alternatively, the preparation via the in situ generated triflate is possible. From the corresponding ω-hydroxyalkylcarbonic acid alkyl esters the triflates may be formed with trifluoromethane sulfonic anhydride/2,6-di-tert-butylpyridine in $CH_2Cl_2$ at $0°$ C. These are then reacted with alcohol 1 with 2,6-di-tert-butylpyridine as a base in nitromethane at $60°$ C. to yield ester 2 [following a procedure of Belostotskii and Hassner, Tetrahedron Lett. 35:5075-5076 (1994)] (step a). In the case that V=$OCH_2CO_2R$, the methylene moiety can be either mono- or di-alkylated using lithium bis-(trimethylsilyl)-amide, iodomethane in THF at $-78°$ C.-RT to yield the O-2-propionic acid ester derivative or the O-2-methyl-2-propionic acid ester, respectively.

Saponification of the ester 2 using standard conditions e.g. LiOH or NaOH in EtOH, MeOH or THF for the alkyl esters or TFA or HCl in THF, ether or $CH_2Cl_2$ for tert butyl esters gives the acid 3 (step b). Treatment of the acid 3 with $NR^1R^2$ $(CH_2)_kNR^3H$ and coupling reagents such as EDCI, HOBT, DCC, 2-chloro-1-methyl-pyridinium iodide or BOP and a base such as Huenig's base, $NEt_3$ or NMM in $CH_2Cl_2$, DMF, DMA or dioxane gives amide 4. Alternatively a two-step procedure might be used: treatment of the acid 3 with oxalyl chloride in $CH_2Cl_2$ in the presence of DMF, followed by reaction with the corresponding amine $NR^1R^2(CH_2)_kNR^3H$. If necessary, the residues R' and $R^2$ may be modified as described for compound 4 in scheme 1. In the case that $R^{1'}$ is hydrogen the desired residue $R^1$ may be introduced by alkylation with a reactive alkyl derivative, if necessary in the appropriate protected form. In the case that the reaction was performed with an amine $NHR^{1'}R^{2'}$ in which $R^{1'}$ and/or $R^{2'}$ contain an ester moiety this can be reduced by e.g. $NaBH_4$ in solvents like THF or MeOH to the corresponding hydroxyalkyl derivatives.

In the case that $R^1$ is an hydroxyalkyl moiety, the compound may be treated with alkyl isocyanate in $CH_2Cl_2$ at temperatures between $0°$ C. and RT to yield the desired lower-alkyl-NH—C(O)—O-lower-alkyl derivative.

If $R^5W$ in 4 is a protecting moiety this can be cleaved using TFA in $CH_2Cl_2$ for BOC-groups or by hydrogenation in methanol/HCl with Pd/C for Z-groups. The resulting ammonium salt may be treated according to one of the procedures described before to derive the appropriate $R^5W$ derivative 4. If needed, the aminocyclohexane derivative can be treated with hexamethyldisilazane at reflux, prior to the introduction of the $R^5W$-moiety.

Scheme 4 to scheme 8 describe the synthesis of intermediates for compounds with m>=0 and V=single bond or lower alkylene.

Scheme 4

4-tert-Butoxycarbonyl amino-cyclohexane-carboxylic acid 1 is converted to the derivative 2 by ester formation (e.g. carbonyl-di-imidazole, methanol in THF, step a) and this is followed by direct alkylation using sodium hydride and a reactive alkyl derivative (step b). The ester 3 is BOC deprotected (TFA, $CH_2Cl_2$, step c), transferred into the desired $R^5W$-derivative 4 using one of the methods described previously for compound 4 in scheme 1 (step d). Saponification of 4 using standard conditions e.g. LiOH or NaOH in EtOH, MeOH or THF for the alkyl esters or TFA or HCl in THF, ether or $CH_2Cl_2$ for tert butyl esters gives the acid 5 (step e).

Reduction of the ester 3 or 4 with lithium aluminum hydride yields the alcohol 6 (step f). Swern oxidation of the alcohol 6 gives the corresponding aldehyde 7 (step g). Alternatively, the aldehyde 7 maybe prepared via the Weinrebamide starting from ester 3 or 4 (saponification of the ester using LiOH or NaOH in EtOH, MeOH or THF, followed by treatment with N,O-dimethyl-hydroxyl-amine-hydrochloride with EDCI and HOBT in $CH_2Cl_2$ at RT and reduction by lithium aluminum hydride, step h).

Scheme 5

Cis- or trans-(4-methylaminomethyl-cyclohexyl)-methanol ($R^4$=Me) 2 can be obtained from cis- or trans-(4-hydroxymethyl-cyclohexylmethyl)-carbamic acid tert-butyl ester 1 [U.S. Pat. Nos. 5,843,973 or 6,022,969] by treatment with lithium aluminum hydride in tetrahydrofuran between RT and the reflux temperature of the tetrahydrofuran (Scheme 5, step a). Introduction of a tert-butoxycarbonyl protective function by treatment with di-tert-butyl-dicarbonate in methanol/triethylamine between −10° C. and RT gives compound 3 ($R^4$=Me) (step b). Compound 1 can also be first O-protected and then N-alkylated at the tert-butoxycarbonyl protected amino function with an alkyl halide in the presence of a base like sodium hydride in a solvent like N,N-dimethylformamide, THF or acetonitrile at temperatures between RT and 80° C. to introduce substituents $R^4$; after O-deprotection the compound 3 is obtained (step c). Compound 3 is subsequently oxidized to the corresponding aldehyde 4 by using e.g. Swern conditions: oxalyl chloride/dimethylsulfoxide/triethylamine in dichloromethane, −78° C. to RT (step d). This aldehyde 4 can be oxidized to the desired carboxylic acid 5 using e.g. ruthenium (III) chloride-hydrate, sodium metaperiodate in a mixture of $CCl_4$, water and acetonitrile. Alternatively, the oxidation of compound 3 can be accomplished in one step using ruthenium (III) chloride-hydrate, sodium metaperiodate in a mixture of $CCl_4$, water and acetonitrile to give acid 5 (step e).

Scheme 6

In scheme 6, cis or trans-[4-(tert-butyl-dimethyl-silanyloxymethyl)-cyclohexyl]-methanol 2 is prepared from the corresponding bis-hydroxymethyl cyclohexane derivative 1 by treatment with one equivalent of n-butyl lithium in tetrahydrofuran at −78° C. followed by one equivalent of tert-butyl-dimethyl-chlorosilane at −65° C. to RT (step a). Mesylation of [4-(tert-butyl-dimethyl-silanyloxymethyl)-cyclohexyl]-methanol 2 (methanesulfonyl chloride in dichloromethane and triethylamine at 0-10° C.) gives the corresponding methanesulfonate, which is treated with sodium cyanide in N,N-dimethylformamide at 80° C. to give the cyano compound 3 (step b). Direct reduction of the cyano compound 3 e.g. by hydrogenation with a platinum catalyst in acidic methanol (e.g. in situ formation from $CHCl_3$ in MeOH) gives the primary O-deprotected amine 4 (step c). Treatment of the amino-alcohol 4 first with di-tert-butyl-dicarbonate in dichloromethane in the presence of triethylamine followed by acetic anhydride and pyridine in dichloromethane gives the di-protected compound 5 (step d). Compound 5 can be N-alkylated at the primary tert-butoxycarbonyl protected amino function with an alkyl halide in the presence of a base like sodium hydride in a solvent like N,N-dimethylformamide or acetonitrile at temperatures between RT and 80° C. to introduce substituents $R^4$ and gives, after basic cleavage of the acetate, the primary hydroxy compound 6 (step e). The primary hydroxy compound 6 can be oxidized subsequently to the corresponding aldehyde 7 by using e.g. Swern conditions: oxalyl chloride/dimethylsulfoxide/triethylamine in dichloromethane, −78° C. to RT (step f). This aldehyde 7 can be oxidized to the desired carboxylic acid 8 using e.g. ruthenium (III) chloride-hydrate, sodium metaperiodate in a mixture of $CCl_4$, water and acetonitrile. Alternatively, the oxidation of compound 6 can be accomplished in on step using ruthenium (III) chloride•hydrate, sodium metaperiodate in a mixture of $CCl_4$, water and acetonitrile to give acid 8.

Scheme 7

Scheme 7 depicts an alternative route to aminocyclohexane derivatives 5-7. Compounds 2 may be derived from the corresponding 4-(aminomethyl)benzyl alcohol, 4-(2-aminoethyl)benzyl alcohol, 4-(3-aminopropyl)benzyl alcohol by hydrogenation (step a). Treatment of the amino-alcohol 2 first with di-tert-butyl-dicarbonate in dichloromethane in the presence of triethylamine (step b) followed by acetic anhydride and pyridine in dichloromethane gives the di-protected compound 4 (step c). Compound 4 can be N-alkylated at the primary tert-butoxycarbonyl protected amino function with an alkyl halide in the presence of a base like sodium hydride in a solvent like N,N-dimethylformamide or acetonitrile at temperatures between RT and 80° C. to introduce substituents $R^4$ and gives, after basic cleavage of the acetate, the primary hydroxy compound 5 (step d). The primary hydroxy compound 5 can be oxidized subsequently to the corresponding aldehyde 6 by using e.g. Swern conditions: oxalyl chloride/dimethylsulfoxide/triethylamine in dichloromethane, −78° C. to RT (step e). This aldehyde 6 can be oxidized to the desired carboxylic acid 7 using e.g. ruthenium (III) chloride-hydrate, sodium metaperiodate in a mixture of $CCl_4$, water and acetonitrile. Alternatively, the oxidation of compound 5 can be accomplished in on step using ruthenium (III) chloride-hydrate, sodium metaperiodate in a mixture of $CCl_4$, water and acetonitrile to give acid 7 (step f).

Scheme 8

Scheme 8 describes the synthesis of pure trans-aldehyde building block 8. Optionally $R^4$ substituted cyclohexanol 1 is synthesized by hydrogenation of the corresponding 4-aminophenol, 4-hydroxybenzylamine, tyramine or 3-(4-hydroxyphenyl)propylamine (see also scheme 1). Amine 1 is converted to the N-protected-derivative 2 (e.g. ZCl, $Na_2CO_3$/$THF/H_2O$) (step a). Oxidation with TEMPO (2,2,6,6-tetramethylpiperidine 1-oxyl, radical) and sodium hypochlorite gives ketone 3 (step b). Wittig reaction with (methoxymethyl)triphenylphosphonium chloride 4 in THF and potassium t-butoxide as base gives enolether 5 (step c). If $R^4$=H, modification of the residue is possible at this stage (with $R^4$-halogenide/NaH in DMF or DMA). Hydrolysis of enolether 5 with 1 N HCl in THF at reflux (step d) gives aldehyde 6. The crude aldehyde 6 (as a cis/trans mixture) can be isomerised via bisulfite-adduct 7 (with disodium pyrosulfite in water/TBME, step e). Bisulfite adduct 7 can then be converted to the pure trans-aldehyde 8 with aqueous $Na_2CO_3$ in water/TBME (step f). Reduction or oxidation of the pure trans-aldehyde 8 as described in the previous schemes gives the corresponding alcohol and carboxylic acid, respectively.

Scheme 9

In scheme 9, the synthesis of carbon analogues is depicted. For compounds with m>=0, the synthesis starts from 4-tert-butoxycarbonyl aminoalkyl-cyclohexane-carboxylic acid derivative 1 (schemes 4-8). BOC-deprotection (TFA, $CH_2Cl_2$) or Z-deprotection (hydrogenation) followed by treatment with $R^5W$-derivatives using one of the methods described previously gives compounds of the formula 2 (step a,b). The acid moiety can be treated with hexamethyldisilazane at reflux prior to the introduction of the $R^5W$-moiety.

Compound 2 is converted to the amide 3 (step c) by treatment with $NR^1R^2(CH_2)_kNR^3H$ and coupling reagents such as EDCI, HOBT, DCC, 2-chloro-1-methyl-pyridinium iodide or BOP and a base such as Huenig's base, $NEt_3$, NMM in $CH_2Cl_2$, DMF, DMA or dioxane. Alternatively a two-step procedure might be used: treatment of the acid 1 with oxalyl chloride in $CH_2Cl_2$ in the presence of DMF, followed by reaction with the corresponding amine $NR^1R^2(CH_2)_kNR^3H$. In the case that $R^{1'}$ is hydrogen the desired residue $R^{1'}$ may be introduced by alkylation with a reactive alkyl derivative, if necessary in the appropriate protected form. In the case that the reaction was performed with an amine $NHR^{1'}R^{2'}$ in which $R^{1'}$ and/or $R^{2'}$ contains an ester moiety this can be reduced by e.g. $NaBH_4$ in solvents like THF, MeOH to the corresponding hydroxyalkyl derivatives.

In the case that $R^1$ is an hydroxyalkyl moiety, the compound may be treated with alkyl isocyanate in $CH_2Cl_2$ at temperatures between 0° C. and RT to yield the desired lower-alkyl-NH—C(O)—O-lower-alkyl derivative.

Alternatively, the sequence of steps can be inverted, amide formation prior to introduction of the desired $R^5W$- residue.

For m>=0, V=alkylene, the synthesis starts with the alcohol 4 (see scheme 4-8 for preparation). Reaction of 4 with e.g. methanesulfonyl chloride in dichloromethane and triethylamine gives the corresponding methanesulfonate, which may be treated with sodium cyanide in N,N-dimethylformamide at 80° C. to yield the cyano compound 5 (step d). Reduction of the cyano compound 5 with DIBAH (−78° C. to RT in THF) gives the $C_1$-elongated aldehyde which can be oxidized to the desired carboxylic acid 6 using ruthenium (III) chloride.hydrate, sodium metaperiodate in a mixture of $CCl_4$, water and acetonitrile (step e). The conversion of acid 6 to the final product 3 may be achieved as described previously (steps a,b,c).

For $C_2$-elongation, the aldehyde 7 (see scheme 4-8 for preparation) may be subjected to Horner-Emmons reaction with triethyl phosphonoacetate, sodium methanolate in ethanol to give the unsaturated ester 8 (step f). The unsaturated ester 8 is hydrogenated in the presence of 10% palladium on carbon in methanol prior to saponification of the ester (e.g. LiOH or NaOH in EtOH, MeOH or THF) to give acid 6 (steps g,h). Acid 6 may be converted to compound 3 as described above (steps a,b,c).

For $C_2$ up to $C_1$-elongation, Corey-Fuchs methodology may be used: Therefore, the aldehyde 7 can be treated with triphenylphosphine, tetrabromomethane and triethylamine in $CH_2Cl_2$ at 0° C. to RT to yield 2,2-dibromo-vinyl derivative 9 (step i). Rearrangement with n-BuLi (ca 1.6 M in hexane) in THF at −78° C., followed by reaction with formaldehyde (−78° C. to RT) gives the propargyl alcohol 10 (l=0) [step k, following conditions described in Marshall et al., J. Org. Chem. 61:5729-5735 (1996); and Baker et al., J. Chem. Soc. Perkin Trans. 1:1415-1421 (1990)].

For longer side chains, the rearrangement is performed with n-BuLi (ca 1.6 M in hexane) in THF at −78° C. as described above. This is followed by addition of a cosolvens such as DMPU and reaction of the intermediate with O-protected 1-bromo-alkyl-alcohols (step q; e.g. 1-bromo-n-tetrahydropyaranyloxyalkane) to give the O-protected compounds which after acidic hydrolysis give the desired compounds 10. Oxidation of the primary alcohol using e.g. Jones' reagent gives the acid 11. The acid 11 is converted to compounds 6 by hydrogenation in the presence of Pt/C in a solvent like methanol, ethanol or EtOAc. The conversion of acid 6 to the final product 3 may be achieved as described previously (step a,b,c).

The following tests were carried out in order to determine the activity of the compounds of formula I and their salts.

Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/µl with ethanol and mixed with phosphate buffer-1% BSA (bovine serum albumin). A stock solution of 1 mM test substance in DMSO was diluted to the desired concentration with phosphate buffer-1% BSA. 40 µl of microsomes were mixed with 20 µl of the solution of the test substance and the reaction was subsequently started with 20 µl of the [$^{14}$C]R,S-MOS solution. The final conditions were 0.4 mg/ml of microsomal proteins and 30 µl of [$^{14}$C]R,S-MOS in phosphate buffer, pH 7.4, containing 0.5% albumin, DMSO<0.1% and ethanol<2%, in a total volume of 80 µl.

After 1 hour at 37° C. the reaction was stopped by the addition of 0.6 ml of 10% KOH-methanol, 0.7ml of water and 0.1 ml of hexane:ether (1:1, v/v) which contained 25 µg of non-radioactive MOS and 25 µg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 µl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%, e.g. the compound of Example 1.6 exhibits an inhibition of 61%, the compound of Example 5.4 exhibits an inhibition of 51%, the compound of Example 15.4 exhibits an inhibition of 65% and the compound of Example 22.6 exhibits an inhibition of 56%.

In addition, the test was carried out with different test substance concentrations and subsequently the $IC_{50}$ value was calculated, i.e. the concentration required to reduce the conversion of MOS into lanosterol to 50% of the control value. The preferred compounds of the present invention exhibit $IC_{50}$ values of 1 nM to 10 µM, preferably of 1-100 nM.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Abbreviations used are: BOC=t-butyloxycarbonyl, $CH_2Cl_2$=dichloromethane, DCC=N,N'-dicyclohexylcarbodiimide, DMA=dimethylacetamide, DMAP=4-dimethylamino-pyridine, DMF=dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalent, HOBT=1-hydroxy-benzo-triazole, Huenig's base=$iPr_2NEt$=N-ethyl diisopropylamine, $KH_2PO_4$=potassium dihydrogen, LAH=lithium aluminum hydride, MeOH=methanol, NaH=sodium hydride, NaI=sodium iodide, Red-Al=sodium bis(2-methoxyethoxy) aluminum hydride, RT=room temperature, TBDMSCl=t-butyldimethylsilyl chloride, TBME=t-butyl methyl ether, THF=tetrahydrofuran.

General remarks: All reactions were performed under argon.

Example 1

1.1

To a suspension of 50 g (0.33 mol) of trans-4-aminocyclohexanol•hydrochloride and 77 g (0.726 mol, 2.2 eq) of $Na_2CO_3$ in 650 mL of THF and 150 mL of water, 51.2 mL (0.363 mol, 1.1 eq) of benzyl chloroformate were added at 5° C. over a period of 20 min. The reaction mixture was stirred at RT for 2 h, diluted with EtOAc and the phases were separated. The organic layer was washed with brine, dried over $Na_2SO_4$, filtered and evaporated. Trituration from n-hexane yielded 162.4 g (98%) of trans-4-hydroxy-cyclohexylcarbamic acid benzyl ester as white crystals, MS: 249 (M) [in analogy to: Venuti et al., J.Med.Chem. 30:303-318 (1987)].

1.2

Over a period of 6 h to a suspension of 37.9 g (0.94 mol, 2.0 eq) of LAH in 1.3 L of THF was added a suspension of 117 g (0.47 mol) of trans-4-hydroxy-cyclohexylcarbamic acid benzyl ester in 1 L of THF via a cannula keeping the temperature between 5-10° C. The reaction was refluxed over night and a mixture of $Na_2SO_4$, silica gel and water (160 g, 50 g, 80 mL) was added, stirred for additional 30 min, filtered and concentrated. The crude material was triturated with n-hexane to yield 27.9 g (46%) of trans-4-methylamino-cyclohexanol. Column chromatography of the mother liquor on silica gel yielded additional 17.1 g (28%) of trans-4-methylamino-cyclohexanol as white solid, MS: 129 ($MH^+$) [in analogy to: Venuti et al., J.Med.Chem. 30:303-318 (1987)].

1.3

To 3 g (23.2 mmol) of trans-4-methylamino-cyclohexanol in 120 mL of $CH_2Cl_2$ were added 4.2 mL (24.4 mmol, 1.05 eq) of N,N-diisopropylethylamine followed by 5.96 g (24.4 mmol, 1.05 eq) of 4-(trifluoromethyl)-benzenesulfonyl chloride in 50 mL of $CH_2Cl_2$. The mixture was stirred at RT over night and the organic phase was extracted with 1M $KHSO_4$, followed by 5% $NaHCO_3$ and brine. The combined organic phases were washed with brine, dried over $Na_2SO_4$ and evaporated. Column chromatography on silica gel with n-hexane:-EtOAc 1:1 yielded 6.0 g (77%) of trans-N-(4-hydroxy-cyclohexyl)-N-methyl-4-trifluoro-methyl-benzenesulfonamide as off-white solid, MS: 338 ($MH^+$).

1.4

To a solution of 0.62 g (5.9 mmol) of methyl beta-hydroxypropionate in 4.5 mL of $CH_2Cl_2$ was added 1.4 mL (6.4 mmol, 2.4 eq) of 2,6-di-tert-butylpyridine, followed by 1.03 mL (6.2 mmol, 2.4 eq) of trifluoromethane sulfonic acid anhydride at 0° C. The solution was stirred at that temperature for 2.5 h, was concentrated and the residue was dissolved in 5 mL of nitromethane. To this solution 1 g (2.96 mmol) of trans-N-(4-hydroxy-cyclohexyl)-N-methyl-4-trifluoromethyl-benzenesulfonamide and 1.3 mL (5.9 mmol, 2.0 eq) of 2,6-di-tert-butylpyridine in 10 mL of nitromethane were added. The solution was stirred at 60° C. for 3 h, diluted with EtOAc and 1M KHSO$_4$. The inorganic phase was extracted with EtOAc, the combined organic phases were washed with a saturated aqueous solution of NaHCO$_3$ and brine, were dried over Na$_2$SO$_4$ and evaporated. Column chromatography on silica gel with EtOAc/n-hexane 1:3 gave 1.2 g (95%) of trans-3-{4-[methyl-(4-trifluoromethyl-benzenesulfonyl)-amino]-cyclohexyloxy}-propionic acid methyl ester as light yellow oil, MS: 424 (MH$^+$).

1.5

1.14 g (2.7 mmol) of trans-3-{4-[methyl-(4-trifluoromethyl-benzenesulfonyl)-amino]-cyclohexyloxy}-propionic acid methyl ester in 27 mL of THF were treated with 27 mL of 1 M LiOH at RT for 1 h. By adding 1 M KHSO$_4$ the solution was acidified, and the mixture was extracted with EtOAc. The organic phase was washed with brine, dried over Na$_2$SO$_4$ and evaporated to give 1.1 g (quantitative) of trans-3-{4-[methyl-(4-trifluoromethyl-benzenesulfonyl)-amino]-cyclohexyloxy}-propionic acid as colorless oil, MS: 408 (M–H)$^-$.

1.6

120 mg (0.29 mmol) of trans-3-{4-[methyl-(4-trifluoromethyl-benzenesulfonyl)-amino]-cyclohexyloxy}-propionic acid in 3 mL of CH$_2$Cl$_2$ were treated with 0.057 mL (0.44 mmol, 1.5 eq) of N,N,N'-trimethylethylenediamine and 0.48 mL (0.36 mmol, 1.5 eq) of NMM. The solution was cooled to 0° C. and 73.0 mg (0.38 mmol, 1.3 eq) of EDCI and 9 mg (0.06 mmol, 0.2 eq) of HOBT were added. The mixture was stirred at RT for 2 days, partitioned between CH$_2$Cl$_2$ and a saturated aqueous solution of NaHCO$_3$. The organic phase was washed with brine, dried over Na$_2$SO$_4$ and evaporated. Column chromatography with CH$_2$Cl$_2$:MeOH 9:1 gave 118 mg (82%) of trans-N-(2-dimethylamino-ethyl)-N-methyl-3-{4-[methyl-(4-trifluoromethyl-benzenesulfonyl)-amino]-cyclohexyloxy}-propionamide as colorless oil, MS: 494 (MH$^+$).

1.7

Analogously to example 1.6, from trans-3-{4-[methyl-(4-trifluoromethyl-benzenesulfonyl)-amino]-cyclohexyloxy}-propionic acid and 1-methylpiperazine was prepared trans-N-methyl-N-{4-[3-(4-methyl-piperazin-1-yl)-3-oxo-propoxy]-cyclohexyl}-4-trifluoromethyl-benzenesulfonamide as colorless oil, MS: 492 (MH$^+$).

Example 2

2.1

Analogously to example 1.4, from trans-N-(4-hydroxy-cyclohexyl)-N-methyl-4-trifluoromethyl-benzenesulfonamide and methyl glycolate was prepared trans-{4-[methyl-(4-trifluoromethyl-benzenesulfonyl)-amino]-cyclohexyloxy}-acetic acid methyl ester as light yellow oil, MS: 409 (M–H$^-$).

2.2

Analogously to example 1.5, from trans-{4-[methyl-(4-trifluoromethyl-benzenesulfonyl)-amino]-cyclohexyloxy}-acetic acid methyl ester was prepared trans-{4-[methyl-(4-trifluoromethyl-benzenesulfonyl)-amino]-cyclohexyloxy}-acetic acid as light yellow oil, MS: 394 (M–H$^-$).

2.3

Analogously to example 1.6, from trans-{4-[methyl-(4-trifluoromethyl-benzenesulfonyl)-amino]-cyclohexyloxy}-acetic acid and N,N,N'-trimethylethylenediamine was prepared trans-N-(2-dimethylamino-ethyl)-N-methyl-2-{4-[methyl-(4-trifluoromethyl-benzenesulfonyl)-amino]-cyclohexyloxy}-acetamide as colorless oil, MS: 480 (MH$^+$).

2.4

Analogously to example 1.6, from trans-{4-[methyl-(4-trifluoromethyl-benzenesulfonyl)-amino]-cyclohexyloxy}-acetic acid and 1-methylpiperazine was prepared trans-N-methyl-N-{4-[2-(4-methyl-piperazin-1-yl)-2-oxo-ethoxy]-cyclohexyl}-4-trifluoromethyl-benzenesulfonamide as colorless oil, MS: 478 (MH$^+$).

Example 3

3.1

Analogously to example 1.1, from trans-4-methylamino-cyclohexanol and benzyl chloroformate was prepared trans-(4-hydroxy-cyclohexyl)-methyl-carbamic acid benzyl ester as white solid, MS: 263 (M).

3.2

To a suspension of 15.0 g (57 mmol) of trans-(4-hydroxy-cyclohexyl)-methyl-carbamic acid benzyl ester in 230 mL of toluene were added 16.8 mL (114 mmol, 2 eq) of bromoacetic acid tert-butyl ester and 1.93 g (5.7 mmol, 0.1 eq) of tetra-n-butylammonium hydrogensulfate and 400 mL of 50% aqueous NaOH. The mixture was stirred at RT for 4 h, additional 1.93 g (5.7 mmol, 0.1 eq) of tetra-n-butyl-ammoniumhydrogensulfate and 4.2 mL of bromo-acetic acid tert-butyl ester were added, and stirring was continued over night. The solution was concentrated and acidified by adding 400 mL of 37% HCl. The solution was extracted with EtOAc, the organic phase was washed with brine and dried over Na$_2$SO$_4$. The solvent was removed to yield 18.2 g (quantitative) trans-[4-(benzyloxycarbonyl-methyl-amino)-cyclohexyloxy]-acetic acid as white solid, MS: 320 (M–H)$^-$.

3.3

Analogously to example 1.6, from trans-[4-(benzyloxycarbonyl-methyl-amino)-cyclohexyloxy]-acetic acid and N,N,N'-trimethylethylenediamine was prepared trans-(4-{[(2-dimethylamino-ethyl)-methyl-carbamoyl]-methoxy}-cyclohexyl)-methyl-carbamic acid benzyl ester as colorless oil, MS: 406 (MH$^+$).

3.4

6.24 g (13.38 mmol) of trans-(4-{[(2-dimethylamino-ethyl)-methyl-carbamoyl]-methoxy}-cyclohexyl)-methyl-carbamic acid benzyl ester in 34 mL of EtOAc were hydrogenated in the presence of 0.51 g of 10% Pd/C. After removal of the catalyst and evaporation of the solvent, the residue was redissolved in 50 mL of MeOH and hydrogenated in the presence of 0.4 g of 10% Pd/C. The catalyst was removed by filtration over decalite and the filtrate was concentrated. To the residue ether and aqueous HCl were added and the layers were separated. The inorganic one was washed with ether, 1M NaOH was added and the compound was extracted with CH$_2$Cl$_2$, and mixtures of CH$_2$Cl$_2$/THF (1:1). The combined organic layers were washed with brine and dried over Na$_2$SO$_4$. Evaporation of the solvent yielded 2.7 g (75%) of trans-N-(2-dimethylamino-ethyl)-N-methyl-2-(4-methylamino-cyclohexyloxy)-acetamide as colorless oil, MS: 272 (MH$^+$).

3.5

To 150 mg (0.55 mmol) of trans-N-(2-dimethylaminoethyl)-N-methyl-2-(4-methylamino-cyclohexyloxy)-acetamide in 4 mL of $CH_2Cl_2$ were added 0.14 mL (0.8 mmol, 1.5 eq) of N,N-diisopropylethylamine followed by 0.08 mL (0.58 mmol, 1.1 eq) of 4-bromophenyl chloroformate. The mixture was stirred at RT for 2 h, and the solution was added to a mixture of $NaHCO_3$ solution and $CH_2Cl_2$. The phases were separated and the inorganic one was extracted with $CH_2Cl_2$. The combined organic phases were washed with brine, dried over $Na_2SO_4$ and evaporated. Column chromatography on silica gel with $CH_2Cl_2$:MeOH 9:1 yielded 174 mg (67%) of trans-(4-{[(2-dimethylamino-ethyl)-methyl-carbamoyl]-methoxy}-cyclohexyl)-methyl-carbamic acid 4-bromo-phenyl ester as colorless oil, MS: 470 ($MH^+$, 1Br).

3.6

Analogously to example 3.5, from trans-N-(2-dimethylamino-ethyl)-N-methyl-2-(4-methylamino-cyclohexyloxy)-acetamide and 4-bromophenyl chloroformate was prepared trans-(4-1{[(2-dimethylamino-ethyl)-methyl-carbamoyl]-methoxy}-cyclohexyl)-methyl-carbamic acid 4-chloro-phenyl ester as colorless oil, MS: 426 ($MH^+$, 1Cl).

Example 4

4.1

A solution of 24.33 g (100 mmol) of BOC-trans-1,4-aminocyclohexane carboxylic acid in 500 mL of DMA was cooled to 0° C. and treated with 9.6 g (220 mmol, 2.2 eq) of NaH (55% in oil) over 30 min. The mixture was warmed to RT (1.5 h), cooled to 0° C. again and was treated with 227.1 mL (1600 mmol, 16 eq) of $CH_3I$ and warmed from 0° C. to RT overnight. The reaction mixture was cooled to 0° C., 100 mL of $H_2O$ and 350 mL of 28% aqueous NaOH were added and the mixture was stirred at RT for 1 h (intermediate methylester was hydrolysed, detected with TLC n-hexane/EtOAc 2:1). The reaction was partitioned between $Et_2O$ (×3)/$H_2O$, the aqueous phase was acidified with 10% aqueous $KHSO_4$ and partitioned between $Et_2O$ (×3), washed once with 10% aqueous NaCl, dried over $Na_2SO_4$ and evaporated to yield 23.2 g (90%) of trans-4-(tert-butoxycarbonyl-methyl-amino)-cyclohexanecarboxylic acid, MS: 256 ($M-H^-$).

4.2

A solution of 5.15 g (20.0 mmol) of trans-4-(tert-butoxycarbonyl-methyl-amino)-cyclohexanecarboxylic acid was dissolved in 50 mL of dioxane, cooled to 10° C. and treated with 50 mL (200 mmol, 10 eq) of 4M HCl in dioxane, then warmed to RT overnight. The solution was evaporated to ca. 15 mL, cooled to 0° C. and precipitated with ~100 mL of $Et_2O$. The solid precipitate was filtrated, washed with $Et_2O$ (×3) and dried under reduced pressure to yield 3.76 g (97%) of trans-4-methylamino-cyclohexanecarboxylic acid·HCl, MS: 156 ($M-H^-$), MP: 249° C., dec.

4.3

0.194 g (1.00 mmol) of trans-4-methylamino-cyclohexanecarboxylic acid•HCl were mixed with 2.62 mL (12.58 mmol, 12.6 eq) of hexamethyldisilazane and heated under reflux to 140° C. for 1 h (total time 1.5 h). The solution was evaporated, suspended in THF and treated with 0.245 g (1.00 mmol, 1 eq) of 4-(trifluoromethyl)-benzenesulfonyl chloride at 0° C. and stirred at RT overnight. 1 mL of water was added at RT followed by 2 mL of 1M NaOH. Stirring was continued for 1 h at RT after this aqueous 1M HCl was added. The solution was then partitioned between $Et_2O$ (×3)/$H_2O$, dried over $Na_2SO_4$ and evaporated to yield 0.234 g (64%) of trans-4-[methyl-(4-trifluoromethyl-benzenesulfonyl)-amino]-cyclohexanecarboxylic acid, MS: 364 ($M-H^-$).

4.4

A solution of 0.137 g (0.375 mmol) of trans-4-[methyl-(4-trifluoromethyl-benzenesulfonyl)-amino]-cyclohexanecarboxylic acid in 2 mL of $CH_2Cl_2$ was treated at RT with 1 drop of DMF, followed by 0.035 mL (0.412 mmol, 1.1 eq) of oxalyl chloride within 5 min, and stirring was continued for 90 min. The solution was evaporated, redissolved in 2 mL of $CH_2Cl_2$ and treated with 0.058 mL (0.450 mmol, 1.2 eq) of N,N,N'-trimethylethylenediamine at 0° C. The reaction was kept at RT for 2 h, then partitioned between $Et_2O$ (×3)/aqueous saturated $NaHCO_3$. The organic phases were washed once with 10% aqueous NaCl, dried over $Na_2SO_4$ and evaporated. Purification by flash-chromatography on 8 g of silica gel ($CH_2Cl_2$:MeOH 99:1 to 9:1) gave 0.088 g (53%) of pure trans-4-[methyl-(4-trifluoromethyl-benzenesulfonyl)-amino]-cyclohexanecarboxylic acid (2-dimethylamino-ethyl)-methyl-amide, MS: 450 ($MH^+$), MP: 83° C.

4.5

In analogy to example 4.4, trans-4-[methyl-(4-trifluoromethyl-benzenesulfonyl)-amino]-cyclohexanecarboxylic acid and N,N,N'-trimethyl-1,3-propane-diamine were converted to trans-4-[methyl-(4-trifluoromethyl-benzenesulfonyl)-amino]-cyclohexanecarboxylic acid (3-dimethylamino-propyl)-methyl-amide, MS: 464 ($MH^+$).

Example 5

5.1

In analogy to example 4.1, BOC-tranexamic acid was converted to trans-4-[(tert-butoxycarbonyl-methyl-amino)-methyl]-cyclohexanecarboxylic acid, MS: 270 ($M-H^-$).

5.2

In analogy to example 4.2, trans-4-[(tert-butoxycarbonyl-methyl-amino)-methyl]-cyclohexanecarboxylic acid was converted to trans-4-methylaminomethyl-cyclohexanecarboxylic acid•HCl, MS: 172 ($MH^+$).

5.3

In analogy to example 4.3, trans-4-methylaminomethyl-cyclohexanecarboxylic acid•HCl and 4-chlorophenylchloroformate were converted to trans-4-{[(4-chloro-phenoxy-carbonyl)-methyl-amino]-methyl}-cyclohexanecarboxylic acid, MS: 324 ($M-H^-$, 1Cl).

5.4

In analogy to example 4.4, trans-4-{[(4-chloro-phenoxy-carbonyl)-methyl-amino]-methyl}-cyclohexanecarboxylic acid and N,N,N'-trimethylethylenediamine were converted to trans-{4-[(2-dimethylamino-ethyl)-methyl-carbamoyl]-cyclohexylmethyl}-methyl-carbamic acid 4-chloro-phenyl ester, MS: 410 ($MH^+$, 1Cl).

5.5

In analogy to example 4.4, trans-4-{[(4-chloro-phenoxy-carbonyl)-methyl-amino]-methyl}-cyclohexanecarboxylic acid and N,N,N'-trimethyl-1,3-propane-diamine were converted to trans-{4-[(3-dimethylamino-propyl)-methyl-carbamoyl]-cyclohexylmethyl}-methyl-carbamic acid 4-chloro-phenyl ester, MS: 424 ($MH^+$, 1Cl).

Example 6

6.1

At −60° C. to −67° C. to a solution of 30.0 g (208 mmol) of trans-(4-hydroxymethyl-cyclohexyl)-methanol in 450 mL of tetrahydrofuran was added 130 mL (208 mmol, 1 eq) of 1.6 M n-butyllithium solution (1.6M in n-hexane) within 30 min. After stirring at −78° C. for 30 min 32.3 g (208 mmol, 1 eq) of tert-butyl-dimethyl-chlorosilane were added within 10 min. Stirring was continued at −65° C. for 15 min. The reaction mixture was allowed to reach RT over night and was then partitioned between ether, 1M HCl solution and water. The organic layer was dried over $MgSO_4$, concentrated under reduced pressure and the residue then chromatographed on silica gel with a 3:1 v/v mixture of n-hexane and EtOAc as the eluent giving 27.7 g (51%) of pure trans-[4-(tert-butyl-dimethyl-silanyloxymethyl)-cyclohexyl]-methanol as colorless viscous oil, MS: 259 ($MH^+$).

6.2

To an ice-cooled solution of 27.6 g (107 mmol) of trans-[4-(tert-butyl-dimethyl-silanyloxymethyl)-cyclohexyl]-methanol and 9.99 mL (128 mmol, 1.2 eq) of methanesulfonyl chloride in 350 mL of $CH_2Cl_2$ were added under stirring at 0-10° C. 29.6 mL (213 mmol, 2 eq) of $Et_3N$ within 20 min. The reaction mixture was then stirred at RT for 1 h. It was then partitioned between $CH_2Cl_2$, 1M HCl and water. The $CH_2Cl_2$-phase was dried over $MgSO_4$ and concentrated to yield 38.2 g of crude trans-methanesulfonic acid 4-(tert-butyl-dimethyl-silanyloxymethyl)-cyclohexylmethyl ester as colorless viscous oil, MS: 354 ($M+NH_4+$).

6.3

38.2 g of crude trans-methanesulfonic acid 4-(tert-butyl-dimethyl-silanyloxymethyl)-cyclohexylmethyl ester and 16.7 g (340 mmol, 3.2 eq) of sodium cyanide dissolved in 380 mL of DMF were stirred at 80° C. for 2 h. After cooling the reaction mixture down to RT, it was partitioned between ether and water. The organic layer was dried over $MgSO_4$ and concentrated under reduced pressure. The residue was chromatographed on silica gel with a 9:1 v/v mixture of n-hexane and EtOAc as the eluent giving 24.2 g (80% over two steps) of pure trans-[4-(tert-butyl-dimethyl-silanyloxymethyl)-cyclohexyl]-acetonitrile as colorless viscous oil, MS: 290 ($MNa^+$).

6.4

A solution of 24.2 g (90.5 mmol) of trans-[4-(tert-butyl-dimethyl-silanyloxymethyl)-cyclohexyl]-acetonitrile, 22 mL (270 mmol, 3 eq) of $CHCl_3$ and 2.4 g of $PtO_2$ (Degussa 223) in 250 mL of ethanol was stirred at RT for 20 h under a hydrogen atmosphere. The catalyst was then removed by filtration and the solvent evaporated under reduced pressure giving 17.1 g (97%) of pure trans-[4-(2-amino-ethyl)-cyclohexyl]-methanol•HCl-salt as colorless solid, MS: 158 ($MH^+$).

6.5

At RT to a solution of 17.6 g (90.9 mmol) of trans-[4-(2-amino-ethyl)-cyclohexyl]-methanol•HCl-salt and 13.9 mL (100 mmol, 1.1 eq) of $Et_3N$ in 120 mL of $CH_2Cl_2$ was added a solution of 21.8 g (100 mmol, 1.1 eq) of di-tert-butyl-dicarbonate in 70 mL of $CH_2Cl_2$ within 10 min. After stirring at RT for 3 h, the reaction mixture was partitioned between $CH_2Cl_2$, 1M HCl solution and water. Then, the $CH_2Cl_2$-phase was dried over $MgSO_4$ and concentrated to yield 27.9 g of crude trans-[2-(4-hydroxymethyl-cyclohexyl)-ethyl]-carbamic acid tert-butyl ester as colorless viscous oil, MS: 275 ($MNH_4^+$).

6.6

A solution of 27.9 g (86.7 mmol) of trans-[2-(4-hydroxymethyl-cyclohexyl)-ethyl]-carbamic acid tert-butyl ester, 41 mL (434 mmol, 5 eq) of acetic anhydride and 35 mL (434 mmol, 5 eq) of pyridine in 140 mL of $CH_2Cl_2$ was stirred at RT for 16 h. The reaction mixture was then taken up in ether and washed with 1M HCl solution, sodium hydrogen carbonate solution and water. Then, the ether-phase was dried over $MgSO_4$ and concentrated to yield 26.0 g crude trans-acetic acid 4-(2-tert-butoxycarbonylamino-ethyl)-cyclohexylmethyl ester as colorless viscous oil, MS: 200 [(M-(tert-butoxycarbonyl))$H^+$].

6.7

To an ice-cooled and stirred solution of the crude 26.0 g trans-acetic acid 4-(2-tert-butoxycarbonylamino-ethyl)-cyclohexylmethyl ester and 5.77 mL (92.6 mmol, 1.1 eq) of $CH_3I$ in 300 mL of DMF was added within 15 min 4.04 g (92.58 mmol, 1.1 eq) of NaH (55% in oil). After stirring at RT over night, additional 1.65 mL (26.5 mmol, 0.3 eq) of $CH_3I$ and 1.16 g (26.5 mmol, 0.3 eq) of NaH were added and the reaction mixture was then stirred at RT for another 1 h. It was then partitioned between ether, 1M HCl solution and water. The organic layer was dried over $MgSO_4$, concentrated under reduced pressure and the residue was then chromatographed on silica gel with a 4:1 v/v mixture of n-hexane and EtOAc as the eluent giving 18.7 g (68% over 3 steps) of pure trans-acetic acid 4-[2-(tert-butoxycarbonyl-methyl-amino)-ethyl]-cyclohexylmethyl ester as colorless viscous oil, MS: 214 [(M-(tert-butoxycarbonyl))$H^+$].

6.8

To a cooled (~15° C.) and stirred solution of 18 g (57.4 mmol) of trans-acetic acid 4-[2-(tert-butoxycarbonyl-methyl-amino)-ethyl]-cyclohexylmethyl ester in 135 ml of dioxane was added 63.2 mL (63.2 mmol, 1.1 eq) of aqueous 1 M NaOH within 5 min. The reaction was homogenised with 13 mL of MeOH and 28.7 mL (28.7 mmol, 0.5 eq) of aqueous 1 M NaOH after 3 h, then stirred for additional 1.5 h. The reaction was evaporated to remove the dioxane, partitioned between $Et_2O$ (×3)/$H_2O$, dried over $Na_2SO_4$ and evaporated to yield 17.13 g (quantitative) of trans-[2-(4-hydroxymethyl-cyclohexyl)-ethyl]-methyl-carbamic acid tert-butyl ester, MS: 272 ($MH^+$).

6.9

A solution of 17.1 g (63.1 mmol) of trans-[2-(4-hydroxymethyl-cyclohexyl)-ethyl]-methyl-carbamic acid tert-butyl ester in 60 mL of $CCl_4$, 60 mL of water and 90 mL of acetonitrile were treated with 0.075 g (0.33mmol, 0.05 eq) of ruthenium (III) chloride•hydrate and 55.4 g (259 mmol, 4.1 eq) of sodium metaperiodate within 30 min. After 6 h the reaction was decanted and washed with $CH_2Cl_2$ (×3). The decanted phase was partitioned between $CH_2Cl_2$ (×3)/$H_2O$, dried over $Na_2SO_4$ and evaporated to yield 17.24 g (96%) of trans-4-[2-(tert-butoxycarbonyl-methyl-amino)-ethyl]-cyclohexanecarboxylic acid, MS: 284 ($M-H^-$).

6.10

In analogy to example 4.2, trans-4-[2-(tert-butoxycarbonyl-methyl-amino)-ethyl]-cyclohexanecarboxylic acid was converted to trans-4-(2-methylamino-ethyl)-cyclohexanecarboxylic acid•HCl, MS: 186 ($MH^+$), MP: 212-214° C.

6.11

In analogy to example 4.3, trans-4-(2-methylamino-ethyl)-cyclohexanecarboxylic acid•HCl and 4-chlorophenylchloroformate were converted to trans-4-{2-[(4-chlorophenoxycarbonyl)-methyl-amino]-ethyl}-cyclohexanecarboxylic acid, MS: 338 ($M-H^-$, 1Cl).

6.12

In analogy to example 4.4, trans-4-{2-[(4-chloro-phenoxy-carbonyl)-methyl-amino]-ethyl}-cyclohexanecarboxylic acid and N,N,N'-trimethylethylenediamine were converted to trans-(2-{4-[(2-dimethylamino-ethyl)-methyl-carbamoyl]-cyclohexyl}-ethyl)-methyl-carbamic acid 4-chloro-phenyl ester, MS: 424 (MH$^+$, 1Cl).

6.13

In analogy to example 4.4, trans-4-{2-[(4-chloro-phenoxy-carbonyl)-methyl-amino]-ethyl}-cyclohexanecarboxylic acid and 2-(1,4-diazepan-1-yl)ethan-1-ol were converted to trans-(2-{4-[4-(2-hydroxy-ethyl)-[1,4]diazepane-1-carbonyl]-cyclohexyl}-ethyl)-methyl-carbamic acid 4-chloro-phenyl ester, MS: 466 (MH$^+$, 1Cl).

Example 7

7.1

A mixture of 0.42 g (2.0 mmol) of trans-4-methylaminomethyl-cyclohexanecarboxylic acid•HCl, 1.85 mL (1.1 mmol) of Huenig's base and 0.57 g (2.4 mmol) of 2,5-dibromo-pyrimidine [Brown and Arantz, J. Chem. Soc. C Issue 10, 1889-1891 (1971)] in 2 mL of DMA was placed in the microwave and heated to 120° C. for 1 h. The solvent was evaporated, partitioned between Et$_2$O (×3)/aqueous 10% KH$_2$PO$_4$, dried over Na$_2$SO$_4$ and evaporated to yield 0.604 g (92%) of trans-4-{[(5-bromo-pyrimidin-2-yl)-methyl-amino]-methyl}-cyclohexanecarboxylic acid, MS: 326 (M–H$^-$, 1Br), MP: 172-174° C.

7.2

In analogy to example 4.4, trans-4-{[(5-bromo-pyrimidin-2-yl)-methyl-amino]-methyl}-cyclohexanecarboxylic acid and N,N,N'-trimethylethylenediamine were converted to trans-4-{[(5-bromo-pyrimidin-2-yl)-methyl-amino]-methyl}-cyclohexanecarboxylic acid (2-dimethylamino-ethyl)-methyl-amide, MS: 412 (MH$^+$, 1Br), MP: 111-113° C.

7.3

In analogy to example 4.4, trans-4-{[(5-bromo-pyrimidin-2-yl)-methyl-amino]-methyl}-cyclohexanecarboxylic acid and N,N,N'-trimethyl-1,3-propane-diamine were converted to trans-4-1{[(5-bromo-pyrimidin-2-yl)-methyl-amino]-methyl}-cyclohexanecarboxylic acid (3-dimethylamino-propyl)-methyl-amide, MS: 426 (MH$^+$, 1Br).

7.4

In analogy to example 4.4, trans-4-{[(5-bromo-pyrimidin-2-yl)-methyl-amino]-methyl}-cyclohexanecarboxylic acid and 1-methyl homopiperazine were converted to trans-(4-{[(5-bromo-pyrimidin-2-yl)-methyl-amino]-methyl}-cyclohexyl)-(4-methyl-[1,4]diazepan-1-yl)-methanone, MS: 424 (MH$^+$, 1Br), MP: 114-116° C.

7.5

In analogy to example 4.4, trans-4-{[(5-bromo-pyrimidin-2-yl)-methyl-amino]-methyl}-cyclohexanecarboxylic acid and 2-(1,4-diazepan-1-yl)ethan-1-ol were converted to trans-(4-{[(5-bromo-pyrimidin-2-yl)-methyl-amino]-methyl}-cyclohexyl)-[4-(2-hydroxy-ethyl)-[1,4]diazepan-1-yl]-methanone, MS: 454 (MH$^+$, 1Br).

Example 8

8.1

In analogy to example 7.1, trans-4-(2-methylamino-ethyl)-cyclohexanecarboxylic acid•HCl and 5-bromo-2-chloropyrimidine were converted to trans-4-{2-[(5-bromo-pyrimidin-2-yl)-methyl-amino)-ethyl}-cyclohexanecarboxylic acid, MS: 340 (M–H$^-$, 1Br), MP: 155-158° C.

8.2

In analogy to example 4.4, trans-4-{2-[(5-bromo-pyrimidin-2-yl)-methyl-amino]-ethyl}-cyclohexanecarboxylic acid and N,N,N'-trimethylethylenediamine were converted to trans-4-{2-[(5-bromo-pyrimidin-2-yl)-methyl-amino]-ethyl}-cyclohexanecarboxylic acid (2-dimethylamino-ethyl)-methyl-amide, MS: 426 (MH$^+$, 1Br), MP: 58-59° C.

8.3

In analogy to example 4.4, trans-4-{2-[(5-bromo-pyrimidin-2-yl)-methyl-amino]-ethyl}-cyclohexanecarboxylic acid and 1-methyl homopiperazine were converted to trans-(4-{2-[(5-bromo-pyrimidin-2-yl)-methyl-amino]-ethyl}-cyclohexyl)-(4-methyl-[1,4]diazepan-1-yl)-methanone, MS: 438 (MH$^+$, 1Br).

8.4

In analogy to example 4.4, trans-4-{2-[(5-bromo-pyrimidin-2-yl)-methyl-amino]-ethyl}-cyclohexanecarboxylic acid and 2-(1,4-diazepan-1-yl)ethan-1-ol were converted to trans-(4-{2-[(5-bromo-pyrimidin-2-yl)-methyl-amino]-ethyl}-cyclohexyl)-[4-(2-hydroxy-ethyl)-[1,4]diazepan-1-yl]-methanone, MS: 468 (MH$^+$, 1Br).

8.5

A solution of 0.10 g (0.21 mmol) of trans-(4-{2-[(5-bromo-pyrimidin-2-yl)-methyl-amino]-ethyl}-cyclohexyl)-[4-(2-hydroxy-ethyl)-[1,4]diazepan-1-yl]-methanone in 2 mL of CH$_2$Cl$_2$ was cooled (0° C.) and treated with 0.048 mL (0.43 mmol, 2 eq) of N-butyl isocyanate. After 20 h and 48 h the reaction was again cooled (0° C.) and treated with 0.048 mL (0.43 mmol, 2.0 eq) and 0.024 mL (0.21 mmol, 2.0 eq) of N-butyl isocyanate, respectively. The reaction was evaporated and dissolved in 5 mL of CH$_2$Cl$_2$/0.5 mL of MeOH and stirred for 1.5 h. After evaporation, the reaction was purified by flash-chromatography on 5 g silica gel (CH$_2$Cl$_2$:MeOH 99:1 to 4:1) to give 0.081 g (68%) of pure trans-butyl-carbamic acid 2-[4-(4-{2-[(5-bromo-pyrimidin-2-yl)-methyl-amino]-ethyl}-cyclohexanecarbonyl)-[1,4]diazepan-1-yl]-ethyl ester, MS: 567 (MH$^+$, 1Br).

Example 9

9.1

In analogy to example 7.1, trans-4-methylaminomethyl-cyclohexanecarboxylic acid•HCl and 2-chloro-5-ethylpyrimidine (4 eq, 5 h 45 min, 120° C.) were converted to trans-4-{[(5-ethyl-pyrimidin-2-yl)-methyl-amino]-methyl}-cyclohexanecarboxylic acid, MS: 276 (M–H$^-$), MP: 128-130° C.

9.2

In analogy to example 4.4, trans-4-{[(5-ethyl-pyrimidin-2-yl)-methyl-amino]-methyl}-cyclohexanecarboxylic acid and N,N,N'-trimethylethylenediamine were converted to trans-4-{[(5-ethyl-pyrimidin-2-yl)-methyl-amino]-methyl}-cyclohexanecarboxylic acid (2-dimethylamino-ethyl)-methyl-amide, MS: 362 (MH$^+$).

9.3

In analogy to example 4.4, trans-4-{[(5-ethyl-pyrimidin-2-yl)-methyl-amino]-methyl}-cyclohexanecarboxylic acid and 2-(1,4-diazepan-1-yl)ethan-1-ol were converted to trans- (4-{[(5-ethyl-pyrimidin-2-yl)-methyl-amino]-methyl}-cyclohexyl)-[4-(2-hydroxy-ethyl)-[1,4]diazepan-1-yl]-methanone, MS: 404 (MH$^+$).

Example 10

10.1

In analogy to example 7.1, trans-4-(2-methylamino-ethyl)-cyclohexanecarboxylic acid•HCl and 2-chloro-5-ethylpyrimidine (4 eq, 2 h, 120° C.) were converted to trans-4-{2-[(5-ethyl-pyrimidin-2-yl)-methyl-amino]-ethyl}-cyclohexanecarboxylic acid, MS: 290 (M–H$^-$).

10.2

In analogy to example 4.4, trans-4-{2-[(5-ethyl-pyrimidin-2-yl)-methyl-amino]-ethyl}-cyclohexanecarboxylic acid and 2-(1,4-diazepan-1-yl)ethan-1-ol were converted to trans-(4-{2-[(5-ethyl-pyrimidin-2-yl)-methyl-amino]-ethyl}-cyclohexyl)-[4-(2-hydroxy-ethyl)-[1,4]diazepan-1-yl]-methanone, MS: 418 (MH$^+$).

Example 11

11.1

In analogy to example 7.1, trans-4-(2-methylamino-ethyl)-cyclohexanecarboxylic Acid•HCl and 2-chloro-5-propylpyrimidine (4 eq, 2 h, 120° C.) were converted to trans-4-{2-[methyl-(5-propyl-pyrimidin-2-yl)-amino]-ethyl}-cyclohexanecarboxylic acid, MS: 304 (M–H$^-$).

11.2

In analogy to example 4.4, trans-4-{2-[methyl-(5-propyl-pyrimidin-2-yl)-amino]-ethyl}-cyclohexanecarboxylic acid and 2-(1,4-diazepan-1-yl)ethan-1-ol were converted to trans-[4-(2-hydroxy-ethyl)-[1,4]diazepan-1-yl]-(4-{2-[methyl-(5-propyl-pyrimidin-2-yl)-amino]-ethyl}-cyclohexyl)-methanone, MS: 432 (MH$^+$).

Example 12

12.1

In analogy to example 7.1, trans-4-(2-methylamino-ethyl)-cyclohexanecarboxylic acid•HCl and 2-bromo-5-chloropyrimidine [synthesized from 5-chloro-2-hydroxy-pyrimidine in analogy to Brown and Arantz, J. Chem. Soc. C Issue 10:1889-1891 (1971)] (1.7 eq, 2 h, 120° C.) were converted to trans-4-{2-[(5-chloro-pyrimidin-2-yl)-methyl-amino]-ethyl}-cyclohexanecarboxylic acid, MS: 296 (M–H$^-$, 1Cl), MP: 118-120° C.

12.2

In analogy to example 4.4, trans-4-{2-[(5-chloro-pyrimidin-2-yl)-methyl-amino]-ethyl}-cyclohexanecarboxylic acid and N,N,N'-trimethylethylenediamine were converted to trans-4-{2-[(5-chloro-pyrimidin-2-yl)-methyl-amino]-ethyl}-cyclohexanecarboxylic acid (2-dimethylamino-ethyl)-methyl-amide, MS: 382 (MH$^+$, 1Cl).

12.3

In analogy to example 4.4, trans-4-{2-[(5-chloro-pyrimidin-2-yl)-methyl-amino]-ethyl}-cyclohexanecarboxylic acid and 1-methyl homopiperazine were converted to trans-(4-{2-[(5-chloro-pyrimidin-2-yl)-methyl-amino]-ethyl}-cyclohexyl)-(4-methyl-[1,4]diazepan-1-yl)-methanone, MS: 394 (MH$^+$, 1Cl).

12.4

In analogy to example 4.4, trans-4-{2-[(5-chloro-pyrimidin-2-yl)-methyl-amino]-ethyl}-cyclohexanecarboxylic acid and 2-(1,4-diazepan-1-yl)ethan-1-ol were converted to trans-(4-{2-[(5-chloro-pyrimidin-2-yl)-methyl-amino]-ethyl}-cyclohexyl)-[4-(2-hydroxy-ethyl)-[1,4]diazepan-1-yl]-methanone, MS: 424 (MH$^+$, 1Cl).

Example 13

13.1

A solution of 0.250 g (1.13 mmol) of trans-4-(2-methylamino-ethyl)-cyclohexanecarboxylic acid•HCl, 1.04 mL (6.09 mmol, 5.3 eq) of Huenig's base and 0.412 g (2.26 mmol, 2 eq) of 2-chloro-4-(trifluoromethyl)pyrimidine in 4 mL of DMA were reacted at RT for 19 h. The solvent was evaporated and the residue partitioned between Et$_2$O (×3)/aqueous 10% KH$_2$PO$_4$, dried over Na$_2$SO$_4$, and evaporated to yield 0.422 g (quantitative) of trans-4-{2-[methyl-(4-trifluoromethyl-pyrimidin-2-yl)-amino]-ethyl}-cyclohexanecarboxylic acid, MS: 330 (M–H$^-$), MP: 110-112° C.

13.2

In analogy to example 4.4, trans-4-{2-[methyl-(4-trifluoromethyl-pyrimidin-2-yl)-amino]-ethyl}-cyclohexanecarboxylic acid and 1-methyl homopiperazine were converted to trans-(4-methyl-[1,4]diazepan-1-yl)-(4-{2-[methyl-(4-trifluoromethyl-pyrimidin-2-yl)-amino]-ethyl}-cyclohexyl)-methanone, MS: 428 (MH$^+$).

Example 14

14.1

A solution of 0.50 g (1.52 mmol) of trans-4-{[(5-bromo-pyrimidin-2-yl)-methyl-amino]-methyl}-cyclohexanecarboxylic acid in 4.5 mL of CH$_2$Cl$_2$ was treated at RT with 1 drop of DMF followed by 0.14 mL (1.68 mmol, 1.1 eq) of oxalyl chloride within 5 min, and stirring was continued for 90 min. The solution was evaporated, the residue was redissolved in CH$_2$Cl$_2$ and added dropwise to a solution of 2.14 mL (30.47 mmol, 20 eq) of cyclopropylamine in 3 mL of CH$_2$Cl$_2$ at 0° C. The reaction was warmed to RT and left for 3 h, then partitioned between Et$_2$O (×3)/aqueous 10% NaHCO$_3$, washed once with aqueous 10% NaHCO$_3$, dried over Na$_2$SO$_4$ and evaporated to yield 0.55g (99%) of trans-4-{[(5-bromo-pyrimidin-2-yl)-methyl-amino]-methyl}-cyclohexanecarboxylic acid cyclopropylamide, MS: 367 (MH$^+$, 1Br).

14.2

0.12 g (0.33 mmol) of trans-4-{[(5-bromo-pyrimidin-2-yl)-methyl-amino]-methyl}-cyclohexanecarboxylic acid cyclopropylamide was dissolved in 10 mL of DMA and treated with 0.21 g (4.90 mmol, 14 eq) of NaH (55% in oil) at 0° C. then warmed to RT. The mixture was then treated with 0.47 g (3.27 mmol, 10 eq) of N-(2-chlorethyl)-N,N-dimethylammonium chloride at 0° C. and warmed to RT. The reaction was stirred for 27 h, then partitioned between Et$_2$O (×3)/ aqueous 10% NaHCO$_3$, washed once with aqueous 10% NaCl, dried over Na$_2$SO$_4$ and evaporated. The residue was chromatographed on silica gel (20g) with CH$_2$Cl$_2$:MeOH 95:5 to yield 0.09 g (68% over 2 steps) of pure trans-4-{[(5-bromo-pyrimidin-2-yl)-methyl-amino]-methyl}-cyclohexanecarboxylic acid cyclopropyl-(2-dimethylamino-ethyl)-amide, MS: 438 (MH$^+$, 1Br).

14.3

In analogy to example 14.1 and 14.2, trans-4-{[(5-ethyl-pyrimidin-2-yl)-methyl-amino]-methyl}-cyclohexanecarboxylic cyclopropylamine and N-(2-chlorethyl)-N,N-dimethylammonium chloride were converted to trans-4-{[(5-ethyl-pyrimidin-2-yl)-methyl-amino]-methyl}-cyclohexanecarboxylic acid cyclopropyl-(2-dimethylamino-ethyl)-amide, MS: 388 (MH$^+$).

14.4

In analogy to example 14.1 and 14.2, trans-4-{[(5-ethyl-pyrimidin-2-yl)-methyl-amino]-methyl}-cyclohexanecarboxylic acid, 2,2,2-trifluoroethylamine and N-(2-chlorethyl)-N,N-dimethylammonium chloride were converted to trans-4-{[(5-ethyl-pyrimidin-2-yl)-methyl-amino]-methyl}-cyclohexanecarboxylic acid (2-dimethylamino-ethyl)-(2,2,2-trifluoroethyl)-amide, MS: 430 (MH$^+$).

Example 15

15.1

A solution of 20.0 g (266.3 mmol) of 2-(methylamino) ethanol was dissolved in 100 mL of CH$_2$Cl$_2$ and treated first with 74.23 mL (532.54 mmol, 2 eq) of Et$_3$N then with 33.8 mL (239.64 mmol, 0.9 eq) of benzylchloroformate within a period of 1.5 h at RT. The reaction was partitioned between Et$_2$O (×3)/aqueous 10% KHSO$_4$ (×2), dried over Na$_2$SO$_4$ and evaporated to yield 37.93 g (68%) of (2-hydroxy-ethyl)-methyl-carbamic acid benzyl ester, MS: 210 (MH$^+$).

15.2

At 0° C. a solution of 18.0 g (86.02 mmol) (2-hydroxy-ethyl)-methyl-carbamic acid benzyl ester was dissolved in 600 mL of CH$_2$Cl$_2$ and treated with 7.35 mL (94.63 mmol, 1.1 eq) of methane sulfonyl chloride and 10.38 mL (129.03 mmol, 1.5 eq) of pyridine. The solution was stirred at RT for 24 h, and then treated again with 4.68 mL (60.22 mmol, 0.7 eq) of methane sulfonyl chloride and 6.23 mL (77.42 mmol, 0.9 eq) of pyridine (0° C.). After 5 h at RT the reaction was evaporated and dried.

The crude mesylate was dissolved in 500 mL of DMA and treated with 83.9 mL (86.03 mmol, 1 eq) of 2-ethylaminoethanol and a catalytic amount of NaI and reacted at RT for 20 h and at 60° C. for 4 h. Additional 41.95 mL (43.02 mmol, 0.5 eq) of 2-ethylaminoethanol were added and reacted at 60° C. for 3 h. Afterwards the solution was evaporated, partitioned between Et$_2$O (×3)/aqueous 10% NaHCO$_3$, dried over Na$_2$SO$_4$ and evaporated. Purification by flash-chromatography on 1.5 kg silica gel (CH$_2$Cl$_2$:MeOH 95:5) gave 17.12 g (71% over 2 steps) of {2-[ethyl-(2-hydroxy-ethyl)-amino]-ethyl}-methyl-carbamic acid benzyl ester, MS: 281 (MH$^+$).

15.3

A solution of 9.71 g (34.65 mmol) of {2-[ethyl-(2-hydroxy-ethyl)-amino]-ethyl}-methyl-carbamic acid benzyl ester was dissolved in 400 mL of MeOH, treated with aqueous 71.03 mL (71.03 mmol, 2 eq) of 1M HCl and put under argon. The solution was treated with 10% Pd/C, and hydrogen. The solution was hydrogenated at normal pressure and ambient temperature over night, filtered, evaporated to ~50 ml and the compound was precipitated with n-pentane to yield 6.84 g (90%) of 2-[ethyl-(2-methylamino-ethyl)-amino]-ethanol•2HCl, MS: 147 (MH$^+$).

15.4

A solution of 0.15 g (0.44 mmol) of trans-4-{2-[(5-bromo-pyrimidin-2-yl)-methyl-amino]-ethyl}-cyclohexanecarboxylic acid in 4 mL of CH$_2$Cl$_2$ was treated at RT with 1 drop of DMF, followed by 0.04 mL (0.48 mmol, 1.1 eq) of oxalyl chloride within 5 min, and stirring was continued for 90 min. The solution was then evaporated, the residue redissolved in acetonitrile and added dropwise to a solution of 0.29 g (1.32 mmol, 3 eq) of 2-[ethyl-(2-methylamino-ethyl)-amino]-ethanol•2HCl and 0.92 mL (6.57 mmol) of Et$_3$N in 4 mL of DMA at 0° C. The reaction was warmed to RT and left overnight, then partitioned between Et$_2$O(×3)/aqueous 10% NaHCO$_3$(2×), dried over Na$_2$SO$_4$ and evaporated then chromatographed over silica gel (20 g) prepared in CH$_2$Cl$_2$: MeOH 97.5:2.5 and eluted in 95:5 to yield 0.13 g (64%) of pure trans-4-{2-[(5-bromo-pyrimidin-2-yl)-methyl-amino]-ethyl}-cyclohexanecarboxylic acid {2-[ethyl-(2-hydroxy-ethyl)-amino]-ethyl}-methyl-amide, MS: 470 (MH$^+$, 1Br).

15.5

In analogy to example 15.4, trans-4-{2-[methyl-(5-propyl-pyrimidin-2-yl)-amino]-ethyl}-cyclohexanecarboxylic acid and 2-[ethyl-(2-methylamino-ethyl)-amino]-ethanol•2HCl were converted to trans-4-{2-[methyl-(5-propyl-pyrimidin-2-yl)-amino]-ethyl}-cyclohexanecarboxylic acid {2-[ethyl-(2-hydroxy-ethyl)-amino]-ethyl}-methyl-amide, MS: 434 (MH$^+$).

15.6

In analogy to example 15.4, trans-4-{2-[(5-chloro-pyrimidin-2-yl)-methyl-amino]-ethyl}-cyclohexanecarboxylic acid and 2-[ethyl-(2-methylamino-ethyl)-amino]-ethanol•2HCl were converted to trans-4-{2-[(5-chloro-pyrimidin-2-yl)-methyl-amino]-ethyl}-cyclohexane-carboxylic acid {2-[ethyl-(2-hydroxy-ethyl)-amino]-ethyl}-methyl-amide, MS: 426 (MH$^+$, 1Cl).

15.7

In analogy to example 15.4, trans-4-{[(5-ethyl-pyrimidin-2-yl)-methyl-amino]-methyl}-cyclohexanecarboxylic acid and 2-[ethyl-(2-methylamino-ethyl)-amino]-ethanol•2HCl were converted to trans-4-{[(5-ethyl-pyrimidin-2-yl)-methyl-amino]-methyl}-cyclohexanecarboxylic acid {2-[ethyl-(2-hydroxy-ethyl)-amino]-ethyl}-methyl-amide, MS: 406 (MH$^+$).

Example 16

16.1

In analogy to example 15.2, (2-hydroxy-ethyl)-methyl-carbamic acid benzyl ester and diethanolamine were converted to {2-[bis-(2-hydroxy-ethyl)-amino]-ethyl}-methyl-carbamic acid benzyl ester, MS: 297 (MH$^+$).

16.2

In analogy to example 15.3, {2-[bis-(2-hydroxy-ethyl)-amino]-ethyl}-methyl-carbamic acid benzyl ester was converted to 2-[(2-hydroxy-ethyl)-(2-methylamino-ethyl)-amino]-ethanol•2HCl, MS: 163 (MHt).

16.3

In analogy to example 15.4, trans-4-{2-[(5-bromo-pyrimidin-2-yl)-methyl-amino]-ethyl}-cyclohexanecarboxylic acid and 2-[(2-hydroxy-ethyl)-(2-methylamino-ethyl)-amino]-ethanol•2HCl were converted to trans-4-{2-[(5-bromo-pyrimidin-2-yl)-methyl-amino]-ethyl}-cyclohexanecarboxylic acid {2-[bis-(2-hydroxy-ethyl)-amino]-ethyl}-methyl-amide, MS: 486 (MH$^+$, 1Br).

16.4

In analogy to example 15.4, trans-4-{2-[(5-chloro-pyrimidin-2-yl)-methyl-amino]-ethyl}-cyclohexanecarboxylic acid and 2-[(2-hydroxy-ethyl)-(2-methylamino-ethyl)-amino]-ethanol•2HCl were converted to trans-4-{2-[(5-chloro-pyrimidin-2-yl)-methyl-amino]-ethyl}-cyclohexanecarboxylic acid {2-[bis-(2-hydroxy-ethyl)-amino]-ethyl}-methyl-amide, MS: 442 (MH$^+$, 1Cl).

Example 17

17.1

16.2 g (62.95 mmol) of trans-4-tert-butoxy carbonylamino-cyclohexanecarboxylic acid methyl ester and 5.87 mL (94.43 mmol, 1.5 eq) of methyl iodide in 100 ml DMF were treated under stirring and ice-cooling with 3.57 g (81.84 mmol, 1.3 eq) of NaH (55% in oil). The solution was stirred at RT for 20 h and then treated under ice-cooling with 1M HCl. The reaction mixture was dissolved in ether and washed 4 times with water. The ether-phases were concentrated under reduced pressure to yield 17.5 g (quantitative) of trans-4-(tert-butoxycarbonyl-methyl-amino)-cyclohexanecarboxylic acid methyl ester, MS: 201 (M–OC$_4$H$_9$).

17.2

In analogy to example 4.2, trans-4-(tert-butoxycarbonyl-methyl-amino)-cyclohexanecarboxylic acid methyl ester gave trans-4-methylamino-cyclohexanecarboxylic acid methyl ester•HCl, MS: 171 (M), MP: 227.7-229.6° C.

17.3

A solution of 2.12 g (10.21 mmol) of trans-4-methylamino-cyclohexanecarboxylic acid methyl ester•HCl was dissolved in 30 mL of pyridine, treated at 0° C. with 1.57 mL (11.23 mmol, 1.1 eq) of 4-chlorophenylchloroformate and stirred for 22 h at RT. The solution was evaporated and partitioned between EtOAc (×3)/aqueous 1M HCl. The organic phases were washed once with aqueous 10% NaCl, dried over Na$_2$SO$_4$ and evaporated to yield 3.41 g (90%) of trans-4-[(4-chloro-phenoxycarbonyl)-methyl-amino]-cyclohexane-carboxylic acid methyl ester, MS: 326 (MH$^+$, 1Cl).

17.4

A solution of 1.1 g (3.37 mmol) of trans-4-[(4-chloro-phenoxycarbonyl)-methyl-amino]-cyclohexanecarboxylic acid methyl ester was dissolved in 25 mL of dioxane and treated at 0° C. with 6.7 mL (6.70 mmol, 2 eq) of aqueous 1M NaOH. After 3 h at RT, the reaction was poured into aqueous 10% KHSO$_4$/Et$_2$O (3×). The organic phases were washed with aqueous 10% NaCl solution and dried over Na$_2$SO$_4$ to give 0.97 g (92%) of trans-4-[(4-chloro-phenoxycarbonyl)-methyl-amino]-cyclohexanecarboxylic acid, MS: 310 (M–H$^-$, 1Cl).

17.5

In analogy to example 4.4, trans-4-[(4-chloro-phenoxycarbonyl)-methyl-amino]-cyclohexanecarboxylic acid and N,N,N'-trimethylethylenediamine were converted to trans-{4-[(2-Dimethylamino-ethyl)-methyl-carbamoyl]-cyclohexyl}-methyl-carbamic acid 4-chlorophenyl ester, MS: 396 (MH$^+$).

Example 18

18.1

In analogy to example 7.1, trans-4-methylamino-cyclohexanecarboxylic acid•HCl and 2,5-dibromo-pyrimidine [Brown and Arantz, J. Chem. Soc. C Issue 10:1889-1891 (1971)] were converted to trans-4-[(5-bromo-pyrimidin-2-yl)-methyl-amino]-cyclohexanecarboxylic acid, MS: 312 (M–H$^-$, 1Br).

18.2

In analogy to example 4.4, trans-4-[(5-bromo-pyrimidin-2-yl)-methyl-amino]-cyclohexanecarboxylic acid and N,N,N'-trimethylethylenediamine were converted to trans-4-[(5-bromo-pyrimidin-2-yl)-methyl-amino]-cyclohexanecarboxylic acid (2-dimethylamino-ethyl)-methyl-amide, MS: 328 (MH$^+$, 1Br).

Example 19

19.1

At –10° C., 2.17 mL (3.57 g, 30 mmol, 3 eq) of thionyl chloride were added to a cooled suspension of 1.57 g (10 mmol) of trans-4-aminomethyl-cyclohexanecarboxylic acid in 20 mL of MeOH. Subsequently the mixture was stirred at RT for 18 h. The solvent was then removed at normal pressure to give 2.07 g (quantitative) of trans-4-aminomethyl-cyclohexanecarboxylic acid methyl ester-hydrochloride as white crystals, MS: 171 (M).

19.2

2.07 g (10 mmol) of trans-4-aminomethyl-cyclohexanecarboxylic acid methyl esters•hydrochloride were suspended in 20 mL of CH$_2$Cl$_2$ and treated with 1.4 mL (10 mmol) of Et$_3$N and 2.88 g (13 mmol, 1.3 eq) of 4-(trifluoromethyl)benzenesulfonyl chloride. The mixture was cooled to –10° C. and 4.14 g (30 mmol, 3 eq) of K$_2$CO$_3$ in 10 mL of H$_2$O were added. The biphasic mixture was stirred vigorously for 10 min at –10° C. and then at RT for 2 h. The aqueous phase was extracted with 2 portions of 20 mL of CH$_2$Cl$_2$. The combined organic phases were washed with H$_2$O and brine, dried over anhydrous Na$_2$SO$_4$ and finally evaporated. The residue was chromatographed on silicagel with CH$_2$Cl$_2$:Et$_2$O (95.5:0.5) as eluent. 3.6 g (95%) of trans-4-[(4-trifluoromethyl-benzenesulfonylamino)-methyl]-cyclohexanecarboxylic acid methyl ester were obtained as white solid, MS: 378 (M–H$^-$).

19.3

A solution of 1.09 g (2.87 mmol) of trans-4-[(4-trifluoromethyl-benzenesulfonylamino)-methyl]-cyclohexanecarboxylic acid methyl ester and 569 mg (85%, 8.62 mmol, 3 eq) of KOH in 20 mL of MeOH and 1 mL of H$_2$O were refluxed for 3 h. After cooling to RT, 4.5 mL of 2M aqueous HCl were added and extracted with 3 portions of 20 mL of CH$_2$Cl$_2$. The combined organic phases were washed with H$_2$O, then with brine, dried over anhydrous Na$_2$SO$_4$ and finally evaporated, leaving 1 g (95%) of trans-4-[(4-trifluoromethyl-benzenesulfonylamino)-methyl]-cyclohexanecarboxylic acid as white solid, MS: 364 ((M–H)$^-$).

19.4

200 mg (0.54 mmol) of trans-4-[(4-trifluoromethyl-benzenesulfonylamino)-methyl]-cyclohexanecarboxylic acid, 210 mg (1.09 mmol, 2 eq) of EDCI, 221 mg (2.2 mmol, 4 eq) of Et$_3$N and 274 mg (2.74 mmol, 5 eq) of 1-methyl-piperazine were dissolved in 5 mL of CH$_2$Cl$_2$. After 70 h reaction at RT, 1 mL of H$_2$O was added and the reaction mixture was stirred vigorously for 1 h. The organic phase was separated, the aqueous phase was extracted with 10 mL of CH$_2$Cl$_2$ and the combined organic phases were washed with H$_2$O and brine. After drying over anhydrous Na$_2$SO$_4$, the organic phase was evaporated. The residue was chromatographed on silicagel with CH$_2$Cl$_2$:MeOH:25% NH$_4$OH (9:1:0.1) as eluent. 120 mg (49%) of trans-N-[4-(4-methyl-piperazine-1-carbonyl)-cyclohexylmethyl]-4-trifluoromethyl-benzenesulfonamide were obtained as colorless amorphous solid, MS: 448 (MH$^+$).

Example 20

20.1

100 mg (4 mmol, 1.1 eq) of sodium were reacted in 2 mL of MeOH. Then 1.33 g (3.5 mmol) of trans-4-[(4-trifluoromethyl-benzenesulfonylamino)-methyl]-cyclohexane carboxylic acid methyl ester dissolved in 3 mL of dry DMF were added, followed by 0.44 mL (7 mmol, 2 eq) of $CH_3I$. The mixture was stirred at RT for 2 h, then poured into ice-water and extracted with 3 portions of 15 mL of $CH_2Cl_2$. The combined organic phases were washed with $H_2O$ and brine, dried over anhydrous $Na_2SO_4$ and evaporated, leaving 1.34 g (97%) of trans-4-{[methyl-(4-trifluoromethyl-benzenesulfonyl)-amino]-methyl}-cyclohexane-carboxylic acid methyl ester as white solid, MS: 411 (M+NH4$^+$).

20.2

In analogy to example 19.3, trans-4-{[methyl-(4-trifluoromethyl-benzenesulfonyl)-amino]-methyl}-cyclohexane-carboxylic acid methyl ester was saponified to yield trans-4-{[methyl-(4-trifluoromethyl-benzenesulfonyl)-amino]-methyl}-cyclohexanecarboxylic acid as a white solid, MS: 378 (M–H$^-$).

20.3

In analogy to example 19.4, trans-4-{[methyl-(4-trifluoromethyl-benzenesulfonyl)-amino]-methyl}-cyclohexanecarboxylic acid and 1-methyl-piperazine were converted to trans-N-methyl-N-[4-(4-methyl-piperazine-1-carbonyl)-cyclohexyl methyl]-4-trifluoromethyl-benzenesulfonamide, MS: 462 (MH$^+$).

Example 21

21.1

A solution of 200 mg (0.53 mmol) trans-4-{[methyl-(4-trifluoromethyl-benzenesulfonyl)-amino]-methyl}-cyclohexanecarboxylic acid and 125 mg (1.05 mmol, 2 eq) of thionyl chloride in 1 mL of dry $CH_2Cl_2$ were heated at 50° C. for 1 h, then evaporated and dissolved in 1 mL of $CH_2Cl_2$. This solution was added to 269 mg (2.54 mmol, 5 eq) of N,N,N'-trimethylethylenediamine in 1 mL of pyridine at 0° C. and stirred for 2 h at RT. Subsequently the reaction mixture was poured on a mixture of ice and water and extracted with 3 portions of 15 mL of $CH_2Cl_2$. The combined organic phases were washed with $H_2O$, diluted HCl, saturated aqueous $NaHCO_3$ solution and brine, then dried over anhydrous $Na_2SO_4$ and finally evaporated. The residue was chromatographed on silicagel with $CH_2Cl_2$:MeOH:25% $NH_4OH$ (9:1:0.1) as eluent. 195 mg (79.8%) of trans-4-{[methyl-(4-trifluoromethyl-benzenesulfonyl)-amino]-methyl}-cyclohexanecarboxylic acid (2-dimethylamino-ethyl)-methyl-amide were obtained as colorless amorphous solid, MS: 464 (MH$^+$).

21.2

In analogy to example 21.1, trans-4-{[methyl-(4-trifluoromethyl-benzenesulfonyl)-amino]-methyl}-cyclohexanecarboxylic acid and 1-methyl-4-(methylamino)piperidine were converted to trans-4-{[methyl-(4-trifluoromethyl-benzenesulfonyl)-amino]-methyl}-cyclohexanecarboxylic acid methyl-(1-methyl-piperidin-4-yl)-amide as white amorphous solid, MS: 490 (MH$^+$).

Example 22

22.1

A cooled solution (0-5° C.) of 7 g (17.8 mmol) of trans-4-{[methyl-(4-trifluoromethyl-benzenesulfonyl)-amino]-methyl}-cyclohexanecarboxylic acid methyl ester in 40 mL of THF was treated with 7 mL (24.5 mmol, 1.4 eq) of a Red-Al solution (3.5 M in toluene) over 15 min. The reaction was stirred at RT for 1 h, then cooled to –10° C. and treated with 1 mL of $H_2O$ in 10 mL of THF. This was followed by the addition of 40 mL of aqueous 25% HCl. 100 mL of EtOAc were added, and the mixture was stirred until two phases separated clearly. The aqueous phase was extracted again with two portions of 75 mL of EtOAc. The combined organic phases were washed with $H_2O$, saturated aqueous $NaHCO_3$ solution, brine, then dried over anhydrous $Na_2SO_4$ and finally evaporated under reduced pressure. Crystallization from EtOH gave 6.12 g (94%) of trans-N-(4-hydroxymethyl-cyclohexylmethyl)-N-methyl-4-trifluoro-methyl-benzenesulfonamide as white crystals, MS: 366 (MH$^+$).

22.2

0.56 mL (6.57 mmol, 2 eq) of oxalyl chloride in 15 mL of $CH_2Cl_2$ were cooled to –78° C., and treated with 0.51 g (6.57 mmol, 2 eq) of dimethylsulfoxide in 3 mL of $CH_2Cl_2$ for 10 min. Then 1.2 g (3.28 mmol) of trans-N-(4-hydroxymethyl-cyclohexylmethyl)-N-methyl-4-trifluoromethyl-benzenesulfonamide in 10 mL of $CH_2Cl_2$ were added and the reaction mixture was stirred at –78° C. for 10 min. Subsequently 2.3 mL (16 4 mmol, 5 eq) of $Et_3N$ were added at the same temperature, the reaction mixture was stirred for 30 min at –78° C., warmed to RT and stirred for 1 hour. It was then poured into 50 mL of an ice/water mixture and extracted 3 times with 50 mL of $CH_2Cl_2$. The combined $CH_2Cl_2$ phases were washed with dilute HCl, $NaHCO_3$ solution and with water, dried over anhydrous $Na_2SO_4$ and finally evaporated. The residue was chromatographed on silicagel with $CH_2Cl_2$:$Et_2O$ (4:1) as eluent. 1.05 g (88%) of trans-N-(4-formyl-cyclohexylmethyl)-N-methyl-4-trifluoro-methyl-benzenesulfonamide were obtained as white solid, MS: 364 (MH$^+$).

22.3

2 g (5.5 mmol) of trans-N-(4-formyl-cyclohexylmethyl)-N-methyl-4-trifluoromethyl-benzenesulfonamide and 2.2 g (6.6 mmol, 1.2 eq) of methyl (triphenyl-phosphoranylidene) acetate in 25 mL of toluene were stirred at 90° C. for 1 h. The solution was concentrated and chromatographed on silicagel with $CH_2Cl_2$:$Et_2O$ 95:5 as eluent, giving 2.09 g (91%) of trans-3-(4-{[methyl-(4-trifluoromethyl-benzenesulfonyl)-amino]-methyl}-cyclohexyl)-acrylic acid methyl ester as an off white solid which was a mixture of E and Z isomers (98:2), MS: 437 (M+NH$_4^+$).

22.4

1.45 g (3.5 mmol) of trans-3-(4-{[methyl-(4-trifluoromethyl-benzenesulfonyl)-amino]-methyl}-cyclohexyl)-acrylic acid methyl ester in 25 mL of EtOAc were hydrogenated at normal pressure with 5% Pd/C as the catalyst to give 1.4 g (96%) of trans-3-(4-{[methyl-(4-trifluoromethyl-benzenesulfonyl)-amino]-methyl}-cyclohexyl)-propionic acid methyl ester as white solid, MS: 422 (MH$^+$).

22.5

In analogy to example 19.3, trans-3-(4-{[methyl-(4-trifluoromethyl-benzenesulfonyl)-amino]-methyl}-cyclohexyl)-propionic acid methyl ester was saponified to trans-3-(4-{[methyl-(4-trifluoromethyl-benzenesulfonyl)-amino]-methyl}-cyclohexyl)-propionic acid, MS: 406 (M–H$^-$).

22.6

In analogy to example 21.1, trans-3-(4-{[methyl-(4-trifluoromethyl-benzenesulfonyl)-amino]-methyl}-cyclohexyl)-propionic acid and N,N,N'-trimethylethylenediamine gave trans-N-(2-dimethylamino-ethyl)-N-methyl-3-(4-{[methyl-(4-trifluoromethyl-benzenesulfonyl)-amino]-methyl}-cyclohexyl)-propionamide as light yellow solid, MS: 492 (MH$^+$).

22.7

In analogy to example 21.1, trans-3-(4-{[methyl-(4-trifluoromethyl-benzenesulfonyl)-amino]-methyl}-cyclohexyl)-propionic acid and 1-methyl-4-(methylamino)piperidine gave trans-N-methyl-N-(1-methyl-piperidin-4-yl)-3-(4-{[methyl-(4-trifluoromethyl-benzene-sulfonyl)-amino]-methyl}-cyclohexyl)-propionamide as pale yellow solid, MS: 518 (MH$^+$).

Example 23

23.1

To a suspension of 1 g (2.96 mmol) of trans-N-(4-hydroxy-cyclohexyl)-N-methyl-4-trifluoromethyl-benzenesulfonamide in 12 mL of toluene were added 0.9 ml (6.04 mmol, 2 eq) of bromo-acetic acid tert-butyl ester, 100 mg (0.3mmol, 0.1 eq) of tetra-N-butylammonium hydrogensulfate and 12 mL of 50% aqueous NaOH. The mixture was stirred at 500 for 1 h. The organic phase was dissolved in EtOAc, dried over Na$_2$SO$_4$, and the solvent evaporated. Column chromatography on silica gel gave 1.3 g (97%) of trans-{4-[methyl-(4-trifluoromethyl-benzenesulfonyl)-amino]-cyclohexyloxy}-acetic acid tert-butyl ester as an off-white solid, MS: 469 (M+NH$_4^+$).

23.2

A solution of 1.19 g (2.6 mmol) trans-{4-[methyl-(4-trifluoromethyl-benzenesulfonyl)-amino]-cyclohexyloxy}-acetic acid tert-butyl ester in 20 ml of anhydrous THF was cooled to −78° and treated dropwise with a 1M solution of lithium bis-(trimethylsilyl)-amide in THF (6.2 ml, 2.5 eq). The mixture was allowed to reach RT within ca. 1 h and cooled again to −78°. A solution of 0.18 ml (2.9 mmol, 1.1 eq) of iodomethane in 2.5 ml of THF was added and the mixture allowed reach RT within ca. 1 h. After addition of ice, the mixture was extracted with EtOAc, dried over Na$_2$SO$_4$, and the solvent evaporated. Column chromatography on silica gel gave 600 mg (49%) of trans-2-{4-[methyl-(4-trifluoromethyl-benzenesulfonyl)-amino]-cyclohexyloxy}-propionic acid tert-butyl ester as a colorless solid, MS: 483 (M+NH$_4^+$).

23.3

Analogously to example 23.2 from trans-2-{4-[methyl-(4-trifluoromethyl-benzene-sulfonyl)-amino]-cyclohexyloxy}-propionic acid tert-butyl ester was prepared trans-2-methyl-2-{4-[methyl-(4-trifluoromethyl-benzenesulfonyl)-amino]-cyclohexyloxy}-propionic acid tert-butyl ester as a light yellow oil, MS: 497 (M+NH$_4^+$).

23.4

A solution of 300 mg (0.64 mmol) of from trans-2-{4-[methyl-(4-trifluoromethyl-benzenesulfonyl)-amino]-cyclohexyloxy}-propionic acid tert-butyl ester in 3 ml of CH$_2$Cl$_2$ was treated wit 0.5 ml (6.7 mmol, 10 eq) of trifluoroacetic acid and stirred at 40° during 3 h. Evaporation of the solvent gave 266 mg (quantitative) of trans-2-{4-[methyl-(4-trifluoromethyl-benzenesulfonyl)-amino]-cyclohexyloxy}-propionic acid as an off-white solid, MS: 408 (M−H$^-$).

23.5

Analogously to example 23.4, from trans-2-methyl-2-{4-[methyl-(4-trifluoromethyl-benzenesulfonyl)-amino]-cyclohexyloxy}-propionic acid tert-butyl ester were prepared trans-2-methyl-2-{4-[methyl-(4-trifluoromethyl-benzenesulfonyl)-amino]-cyclohexyloxy}-propionic acid as a light brown oil, MS: 422 (M−H$^-$).

23.6

50 mg (0.12 mmol) of trans-2-{4-[methyl-(4-trifluoromethyl-benzenesulfonyl)-amino]-cyclohexyloxy}-propionic acid in 1 ml of CH$_2$Cl$_2$ were treated with 30 mg (0.15 mmol, 1.2 eq) of DCC, 18 mg (0.15 mmol, 1.2 eq) of DMAP, and 19 mg of N,N,N'-trimethylenediamine. The solution was stirred overnight and partitioned between Et$_2$O and 0.5M aqueous NaOH. The organic phase was dried over Na$_2$SO$_4$ and the solvent evaporated. Column chromatography on silica gel gave 10 mg (17%) of trans-N-(2-dimethylamino-ethyl)-N-methyl-2-{4-[methyl-(4-trifluoromethyl-benzenesulfonyl)-amino]-cyclohexyloxy}-propionamide as a light yellow oil, MS: 494 (MH$^+$).

23.7

A solution of 30 mg (0.07 mmol) trans-2-methyl-2-{4-[methyl-(4-trifluoromethyl-benzenesulfonyl)-amino]-cyclohexyloxy}-propionic acid in CH$_2$Cl$_2$ was treated with 22 mg (0.085 mmol, 1.2 eq) of 2-chloro-1-methyl-pyridinium iodide and 11 μl (0.0851.2 eq) of N,N,N'-trimethylenediamine. The mixture was stirred overnight and partitioned between Et$_2$O and 0.5M aqueous NaOH. The organic phase was dried over Na$_2$SO$_4$ and the solvent evaporated. Column chromatography on silica gel gave 20 mg (56%) of trans-N-(2-dimethylamino-ethyl)-2,N-dimethyl-2-{4-[methyl-(4-trifluoromethyl-benzenesulfonyl)-amino]-cyclohexyloxy}-propionamide as colorless oil, MS: 508 (MH$^+$).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed:

1. A compound of formula I

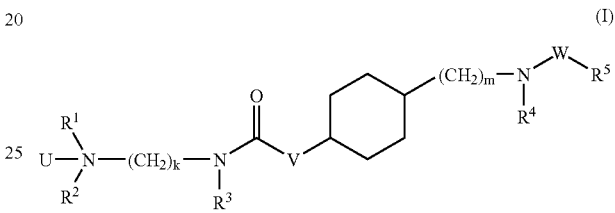

wherein
U is O or a lone pair;
$R^1$ is lower-alkyl, hydroxy-lower-alkyl, cycloalkyl or lower-alkyl-NH—C(O)—O-lower-alkyl;
$R^2$ and $R^3$ are bonded to each other to form a ring together with the N—(CH$_2$)$_k$—N group to which they are attached and —$R^2$—$R^3$— is (CH$_2$)$_3$;
$R^4$ is lower-alkyl;
$R^5$ is substituted or unsubstituted pyrimidine;
W is a single bond;
$R^6$ is hydrogen or lower-alkyl;
V is a single bond, lower-alkylene, or lower-alkylene-oxy;
k 2;
m is 0, 1, 2, or 3, wherein k+m is not more than 5;
and pharmaceutically acceptable salts thereof.

2. The compound of claim 1, wherein said compound is a trans-isomer of formula Ia

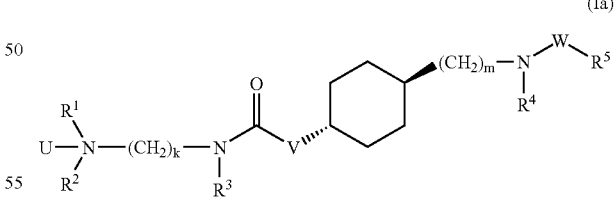

wherein $R^1$, $R^2$, $R^3$, $R^4$, $R^5$, U, V, W, k and m are as defined in claim 1, and pharmaceutically acceptable salts thereof.

3. The compound of claim 2, wherein U is a lone pair.
4. The compound of claim 2, wherein $R^4$ is methyl.
5. The compound of claim 1, wherein V is a single bond, —(CH$_2$)$_2$—, —CH$_2$—O— or —(CH$_2$)$_2$—O—.
6. A compound selected from the group consisting of
trans-(4-{2-[(5-Bromo-pyrimidin-2-yl)-methyl-amino]-ethyl}-cyclohexyl)-(4-methyl-[1,4]diazepan-1-yl)-methanone, trans-(4-{2-[(5-Bromo-pyrimidin-2-yl)-methyl-amino]-ethyl}-cyclohexyl)-[4-(2-hydroxy-ethyl)-[1,4]diazepan-1-yl]-methanone, trans-(4-{2-[(5-Chloro-pyrimidin-2-yl)-methyl-amino]-ethyl}-cyclohexyl)-(4-methyl-[1,4]diazepan-1-yl)-methanone, and and pharmaceutically acceptable salts thereof.

7. A process for the manufacture of a compound of claim 1, which process comprises reacting a compound of formula II

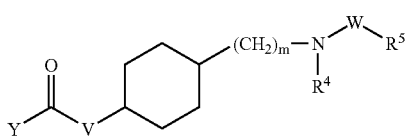

wherein $R^4$, $R^5$, V, W, and m have the significance given in claim 1, and Y is OH, Cl, or Br, with $NR^1R^2(CH_2)_kNR^3H$, wherein $R^1$, $R^2$, $R^3$ and k have the significance given in claim 1, and optionally converting the product to a pharmaceutically acceptable salt, or optionally converting the product, wherein U is a lone pair, to a corresponding compound wherein U is O.

8. A pharmaceutical composition comprising a compound of the formula

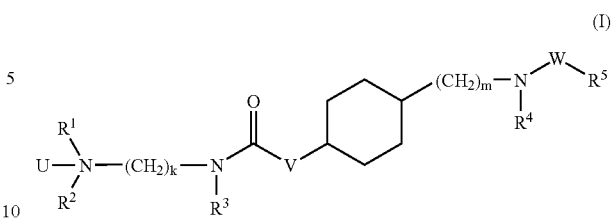

wherein
- U is O or a lone pair;
- $R^1$ is lower-alkyl, hydroxy-lower-alkyl, cycloalkyl or lower-alkyl-NH—C(O)—O-lower-alkyl;
- $R^2$ and $R^3$ are bonded to each other to form a ring together with the N—$(CH_2)_k$—N group to which they are attached and —$R^2$—$R^3$—$(CH_2)_3$;
- $R^4$ is lower-alkyl;
- $R^5$ is substituted or unsubstituted pyrimidine;
- W is a single bond;
- $R^6$ is hydrogen or lower-alkyl;
- V is a single bond, lower-alkylene, or lower-alkylene-oxy;
- k 2;
- m is 0, 1, 2, or 3, wherein k+m is not more than 5;
- and pharmaceutically acceptable salts thereof together with a pharmaceutically acceptable carrier and/or adjuvant.

* * * * *